United States Patent
Braido et al.

(10) Patent No.: US 11,737,870 B2
(45) Date of Patent: Aug. 29, 2023

(54) PROSTHETIC HEART VALVES

(71) Applicant: St. Jude Medical, LLC, Abbott Park, IL (US)

(72) Inventors: Peter N. Braido, Wyoming, MN (US); Yousef F. Alkhatib, Edina, MN (US)

(73) Assignee: St. Jude Medical, LLC, Abbott Park, IL (US)

( * ) Notice: Subject to any disclaimer, the term of this patent is extended or adjusted under 35 U.S.C. 154(b) by 45 days.

(21) Appl. No.: 17/550,339

(22) Filed: Dec. 14, 2021

(65) Prior Publication Data

US 2022/0096225 A1 Mar. 31, 2022

Related U.S. Application Data

(60) Continuation of application No. 16/416,378, filed on May 20, 2019, now Pat. No. 11,229,516, which is a
(Continued)

(51) Int. Cl.
*A61F 2/24* (2006.01)
*A61L 27/36* (2006.01)
*A61L 27/54* (2006.01)

(52) U.S. Cl.
CPC ........ *A61F 2/2418* (2013.01); *A61L 27/3604* (2013.01); *A61L 27/54* (2013.01);
(Continued)

(58) Field of Classification Search
CPC .. A61F 2/89; A61F 2/82; A61F 2/2418; A61F 2/2412; A61F 2/915;
(Continued)

(56) References Cited

U.S. PATENT DOCUMENTS

| 4,343,048 A | * | 8/1982 | Ross | A61F 2/2418 623/2.14 |
| 4,851,000 A | * | 7/1989 | Gupta | A61F 2/2418 623/2.18 |

(Continued)

FOREIGN PATENT DOCUMENTS

| EP | 1690515 A1 | 8/2006 |
| EP | 2316381 A2 | 5/2011 |

(Continued)

OTHER PUBLICATIONS

International Search Report for Application No. PCT/US2008/007015 dated Sep. 8, 2008.

*Primary Examiner* — Seema Mathew
(74) *Attorney, Agent, or Firm* — Sleman & Lund LLP

(57) ABSTRACT

A prosthetic heart valve (e.g., a prosthetic aortic valve) is designed to be somewhat circumferentially collapsible and then re-expandable. The collapsed condition may be used for less invasive delivery of the valve into a patient. When the valve reaches the implant site in the patient, it re-expands to normal operating size, and also to engage surrounding tissue of the patient. The valve includes a stent portion and a ring portion that is substantially concentric with the stent portion but downstream from the stent portion in the direction of blood flow through the implanted valve. When the valve is implanted, the stent portion engages the patient's tissue at or near the native valve annulus, while the ring portion engages tissue downstream from the native valve site (e.g., the aorta).

18 Claims, 30 Drawing Sheets

Related U.S. Application Data division of application No. 14/541,944, filed on Nov. 14, 2014, now abandoned, which is a continuation of application No. 12/451,678, filed as application No. PCT/US2008/007015 on Jun. 4, 2008, now Pat. No. 9,572,660.

(60) Provisional application No. 60/933,274, filed on Jun. 4, 2007.

(52) U.S. Cl.
CPC ........... *A61F 2210/0076* (2013.01); *A61F 2220/0016* (2013.01); *A61F 2220/0075* (2013.01); *A61F 2230/008* (2013.01); *A61F 2230/0054* (2013.01)

(58) Field of Classification Search
CPC .... A61F 2002/825; A61F 2/07; A61F 2/2409; A61F 2/2439; A61F 2250/0063; A61F 2250/0039; A61F 2220/0008; A61F 2220/0016
See application file for complete search history.

(56) References Cited

U.S. PATENT DOCUMENTS

| | | | |
|---|---|---|---|
| 5,957,949 A * | 9/1999 | Leonhardt | A61F 2/07 606/198 |
| 6,767,362 B2 * | 7/2004 | Schreck | A61F 2/2469 623/2.14 |
| 7,857,845 B2 | 12/2010 | Stacchino et al. | |
| 8,317,858 B2 * | 11/2012 | Straubinger | A61F 2/82 623/2.12 |
| 8,425,593 B2 * | 4/2013 | Braido | A61F 2/89 623/2.18 |
| 8,465,540 B2 * | 6/2013 | Straubinger | A61F 2/07 623/1.24 |
| 8,834,563 B2 * | 9/2014 | Righini | A61F 2/2436 623/2.18 |
| 8,840,661 B2 | 9/2014 | Manasse | |
| 8,845,720 B2 * | 9/2014 | Conklin | A61F 2/2412 623/2.14 |
| 9,370,418 B2 | 6/2016 | Pintor et al. | |
| 9,474,604 B2 | 10/2016 | Centola et al. | |
| 9,504,566 B2 | 11/2016 | Guttenberg et al. | |
| 9,579,194 B2 | 2/2017 | Elizondo et al. | |
| 9,744,031 B2 | 8/2017 | Girard et al. | |
| 9,770,327 B2 | 9/2017 | Bruchman et al. | |
| 9,801,711 B2 | 10/2017 | Gainor | |
| 9,987,133 B2 | 6/2018 | Straubinger et al. | |
| 10,321,986 B2 | 6/2019 | Bruchman et al. | |
| 10,376,360 B2 | 8/2019 | Bruchman et al. | |
| 10,413,406 B2 | 9/2019 | Benichou | |
| 10,441,415 B2 | 10/2019 | Johnson et al. | |
| 10,646,333 B2 | 5/2020 | Rothstein | |
| 10,695,170 B2 | 6/2020 | Conklin et al. | |
| 10,993,805 B2 | 5/2021 | Straubinger et al. | |
| 11,109,963 B2 | 9/2021 | Dienno et al. | |
| 11,534,294 B2 * | 12/2022 | Braido | A61F 2/2409 |
| 2001/0021872 A1 * | 9/2001 | Bailey | A61F 2/2469 623/2.18 |
| 2002/0138138 A1 * | 9/2002 | Yang | A61F 2/2427 623/2.38 |
| 2003/0236568 A1 * | 12/2003 | Hojeibane | A61F 2/915 623/2.18 |
| 2004/0093060 A1 * | 5/2004 | Seguin | A61F 2/2418 623/1.11 |
| 2004/0210304 A1 * | 10/2004 | Seguin | A61F 2/2409 623/2.11 |
| 2005/0033398 A1 * | 2/2005 | Seguin | A61F 2/2418 623/1.14 |
| 2005/0043790 A1 * | 2/2005 | Seguin | A61F 2/2418 623/2.18 |
| 2005/0137682 A1 | 6/2005 | Justino | |
| 2005/0137690 A1 | 6/2005 | Salahieh et al. | |
| 2005/0234546 A1 | 10/2005 | Nugent et al. | |
| 2006/0025855 A1 | 2/2006 | Lashinski et al. | |
| 2006/0074484 A1 * | 4/2006 | Huber | A61F 2/2412 623/2.14 |
| 2006/0122692 A1 * | 6/2006 | Gilad | A61F 2/2418 623/1.35 |
| 2006/0149360 A1 * | 7/2006 | Schwammenthal | A61F 2/2418 623/1.36 |
| 2006/0178740 A1 * | 8/2006 | Stacchino | A61F 2/848 623/2.18 |
| 2006/0259137 A1 * | 11/2006 | Artof | A61F 2/243 623/2.11 |
| 2006/0282157 A1 * | 12/2006 | Hill | A61B 90/39 623/1.11 |
| 2007/0043435 A1 * | 2/2007 | Seguin | A61F 2/2433 623/2.11 |
| 2007/0233228 A1 | 10/2007 | Eberhardt et al. | |
| 2007/0282436 A1 * | 12/2007 | Pinchuk | A61F 2/2436 623/2.11 |
| 2007/0288087 A1 * | 12/2007 | Fearnot | A61F 2/2418 623/2.18 |
| 2008/0140189 A1 * | 6/2008 | Nguyen | A61F 2/2427 623/2.11 |
| 2008/0147179 A1 | 6/2008 | Cai et al. | |
| 2009/0062908 A1 * | 3/2009 | Bonhoeffer | A61F 2/2427 623/1.13 |
| 2009/0099653 A1 * | 4/2009 | Suri | A61F 2/2418 623/2.11 |
| 2009/0157175 A1 | 6/2009 | Benichou | |
| 2009/0171456 A1 * | 7/2009 | Kveen | A61F 2/2418 623/2.11 |
| 2009/0287296 A1 * | 11/2009 | Manasse | A61F 2/2418 623/1.26 |
| 2010/0082094 A1 | 4/2010 | Quadri et al. | |
| 2010/0168844 A1 * | 7/2010 | Toomes | A61F 2/2418 623/2.18 |
| 2010/0204781 A1 * | 8/2010 | Alkhatib | A61F 2/2445 623/1.26 |
| 2011/0022157 A1 * | 1/2011 | Essinger | A61F 2/2436 623/1.11 |
| 2011/0160836 A1 | 6/2011 | Behan | |
| 2011/0218619 A1 * | 9/2011 | Benichou | A61F 2/2418 623/2.11 |
| 2012/0253453 A1 * | 10/2012 | Bruchman | A61F 2/2418 623/1.24 |
| 2014/0012371 A1 * | 1/2014 | Li | A61F 2/2418 264/273 |
| 2014/0167308 A1 * | 6/2014 | Li | B29C 41/14 264/306 |
| 2014/0350660 A1 * | 11/2014 | Cocks | A61F 2/2418 623/1.16 |

FOREIGN PATENT DOCUMENTS

| | | |
|---|---|---|
| JP | 2009520535 A | 5/2009 |
| WO | 2005076973 A2 | 8/2005 |
| WO | 2006041505 A1 | 4/2006 |
| WO | 2006127765 A1 | 11/2006 |
| WO | 2008028569 A1 | 3/2008 |

* cited by examiner

PROSTHETIC HEART VALVES

The present application is a continuation of U.S. patent application Ser. No. 16/416,378, filed on May 20, 2019, which is a divisional of U.S. patent application Ser. No. 14/541,944, filed Nov. 14, 2014, which is a continuation of U.S. Pat. No. 9,572,660, filed Nov. 24, 2009, which is a National Phase of PCT Patent Application No. PCT/US2008/007015 filed on Jun. 4, 2008, which claims the benefit of U.S. provisional patent application 60/933,274, filed Jun. 4, 2007, the disclosures of which are hereby incorporated by reference herein.

BACKGROUND OF THE INVENTION

This invention relates to prosthetic heart valves. For the most part, the invention will be illustratively described in the context of a prosthetic aortic valve that can be temporarily collapsed during a portion of the implantation procedure, and that can be subsequently expanded to its full size at the implantation site. The invention is not necessarily limited to this particular type of use, however, and it will be appreciated that various aspects of the invention can be used in other ways and/or in other contexts.

Many people with severe aortic stenosis go untreated because they are not considered to be suitable candidates for aortic valve replacement using the known prostheses and procedures (e.g., open-chest, open-heart surgery). In an attempt to provide ways of treating these patients, collapsible prosthetic valves have been developed for insertion within stenotic aortic valve leaflets in less invasive ways. For example, such less invasive delivery of the prosthetic valve may be via catheter-like, trocar-like, or laparoscopic-type instrumentation. The delivery may be percutaneous (e.g., via vessels of the patient's circulatory system that lead to the aortic valve), or it may be through the wall of the heart (e.g., through the apex of the left ventricle of the heart (i.e., transapically)), etc. It is believed, however, that current designs for prosthetic valves that are to be delivered in ways such as these are in need of improvement with respect to aspects such as (1) long-term durability, (2) the possibility of undesirable impingement on the adjacent mitral valve, (3) paravalvular leakage, etc.

BRIEF SUMMARY OF THE INVENTION

A prosthetic heart valve in accordance with the invention may include an annular supporting structure that has (1) an annular stent portion and (2) a ring portion that is substantially concentric with the stent portion but that is downstream from the stent portion in the direction of blood flow through the valve when the valve is in use in a patient. The stent portion has a blood-outflow region that includes a plurality of annularly spaced commissure tips at which the stent portion is closest to the ring portion. The ring portion is connected to the stent portion substantially solely by flexible strut structures that extend from the stent portion to the ring portion adjacent to the commissure tips. Each of the strut structures starts from a respective point or points on the stent structure that are farther from the ring portion than the commissure tips. The valve further includes a plurality of valve leaflets supported by the stent portion. The ring portion is downstream from the stent portion sufficiently far that the leaflets cannot contact the ring portion.

The supporting structure is preferably annularly compressible and re-expandable. The stent portion is preferably adapted to engage tissue of the patient at or near the native heart valve annulus of the patient. (This engagement may be through other material that has been used to cover the stent portion.) The ring portion is adapted to engage the inside of a blood vessel of the patient downstream from the native heart valve annulus. (Again, this engagement may be through other material that has been used to cover the ring portion.)

The ring portion may be integrally connected to the stent portion. The ring portion and the stent portion may be annularly compressible to substantially the same circumference. The ring portion may be re-expandable to a circumferential size that is greater than the circumferential size of at least a part of the stent portion when the stent portion is re-expanded.

The stent portion may include a skirt portion that is adjacent to the blood inflow end of the valve when the valve is in use in a patient. The skirt portion may re-expand to flare radially out from a remainder of the stent portion. The inflow end of the stent portion (e.g., the skirt) may be scalloped in an annular direction around the heart valve to avoid impingement on another of the patient's heart valves or other structures in the patient's heart.

The supporting structure may include barbs that engage tissue of the patient when the valve is in use.

The ring portion may be constructed so that it is more resistant to annular compression than the stent portion.

The stent portion may include a blood-outflow-edge structure that comprises (1) a first ring member that extends annularly around the valve in a serpentine pattern and that has a relatively large number of connections to other upstream structure of the stent portion, and (2) a second ring member that (a) follows the first ring member annularly around the valve in a similar serpentine pattern, (b) is spaced downstream from the first ring member, and (c) has a relatively small number of connections to the first ring member. The ring portion may be attached to the stent portion by connections between the ring portion and the second ring member. The last-mentioned connections may connect to points on the second ring member that are closest to the ring portion. Portions of each of the leaflets may be inserted between the first and second ring members.

Sheet material (e.g., fabric and/or tissue) may be provided for covering at least part of the stent portion and/or at least part of the ring portion. Any of this sheet material may be attached to the inside and/or outside of the stent portion and/or the ring portion. Such sheet material covering may comprise one layer or more than one layer. Different sheet materials may be used at different locations; and where multiple layers are used, different sheet materials may be used in various combinations in different layers. If the valve includes the above-mentioned first and second ring members, then sheet material (of an above-mentioned type) may be provided for covering the first and/or second ring members. If leaflet portions are inserted between the first and second ring members, then sheet material may be interposed between the leaflets and the first and second ring members.

Further features of the invention, its nature and various advantages, will be more apparent from the accompanying drawings and the following detailed description.

DETAILED DESCRIPTION

Figure 1:
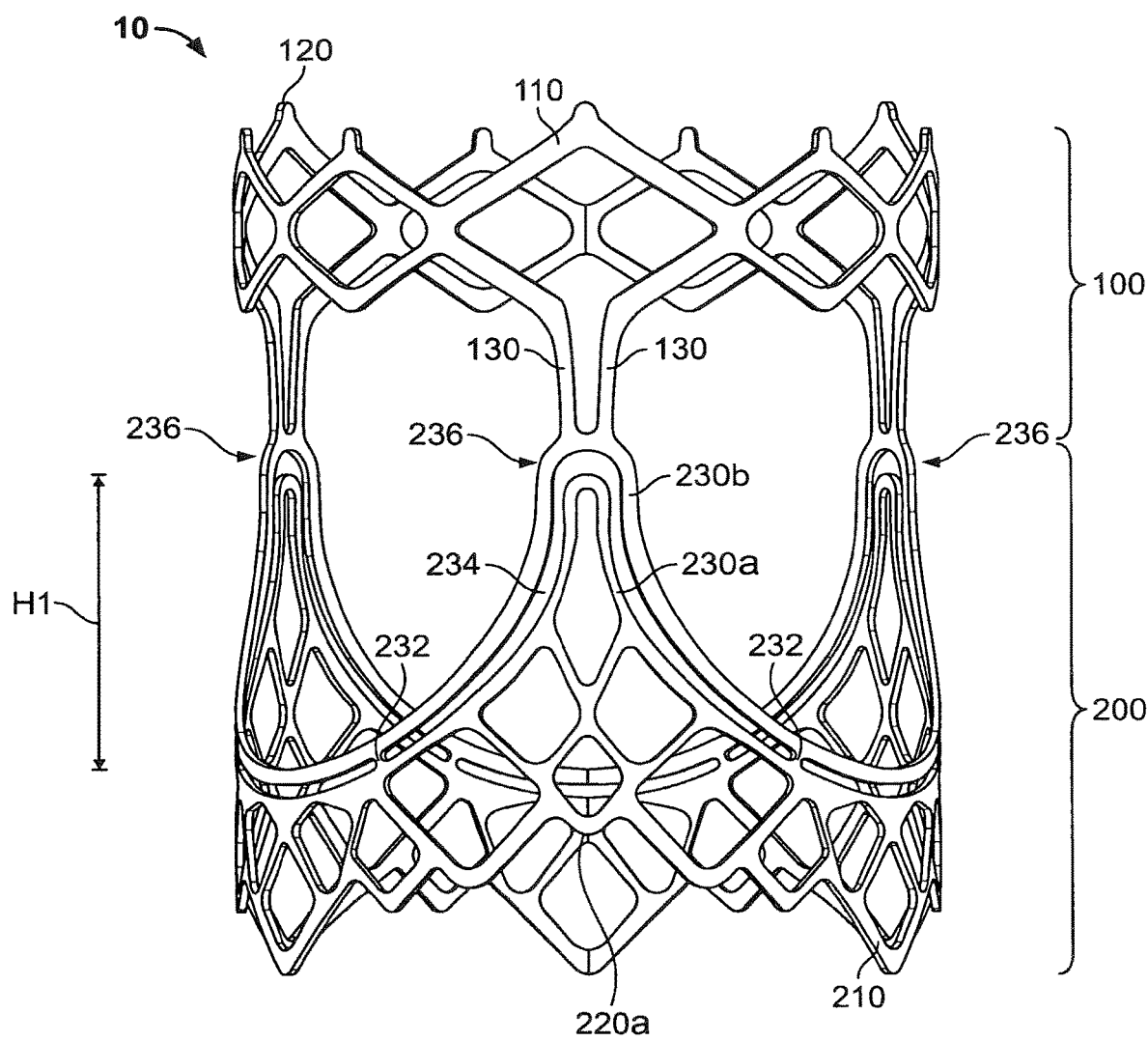
FIG. 1 is a simplified elevational view of an illustrative embodiment of a component of a prosthetic heart valve in accordance with the invention.
Figure 2:
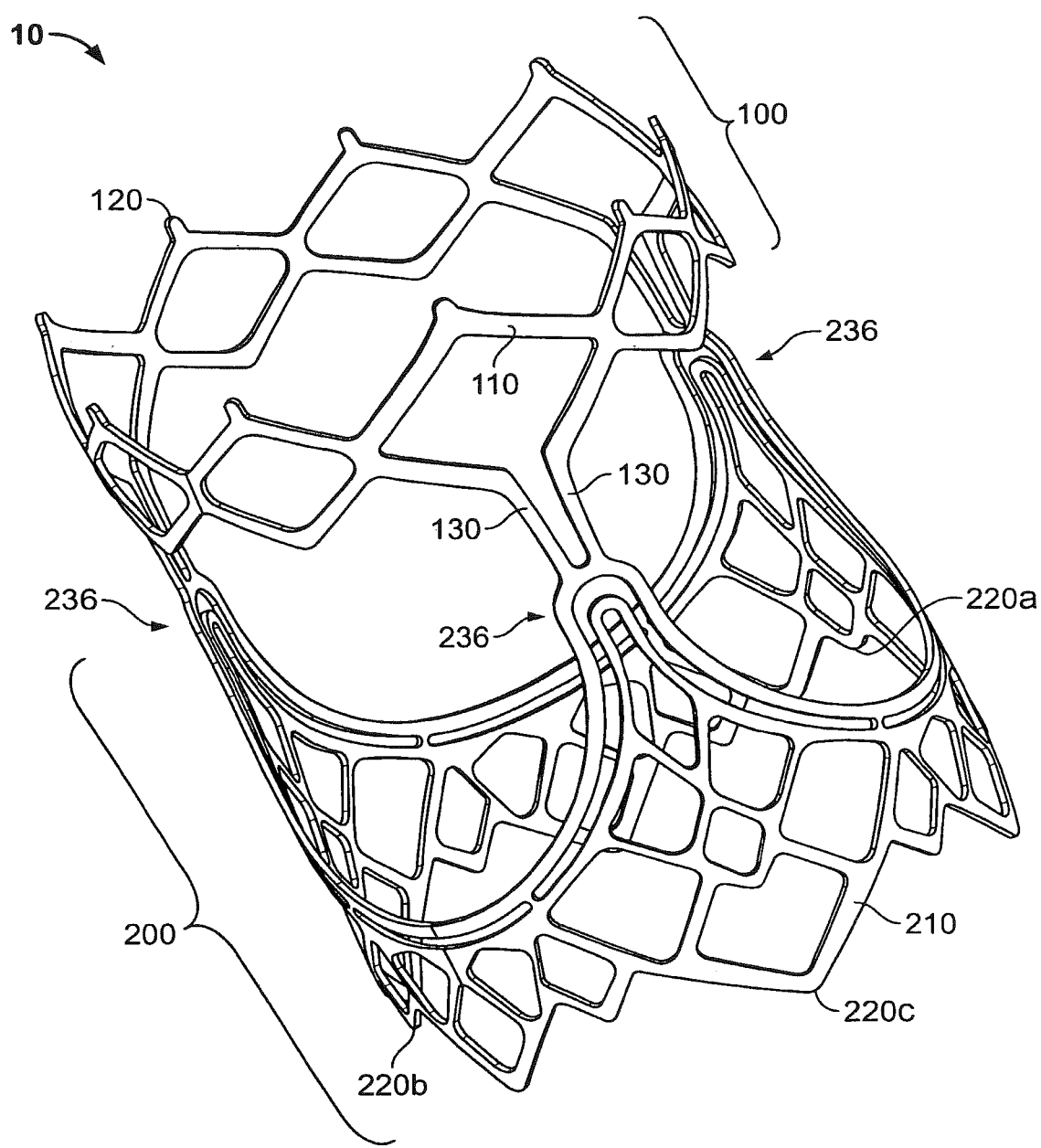
FIG. 2 is a simplified isometric or perspective view of the FIG. 1 component.

This detailed description will begin with discussion of an illustrative embodiment of a primary metal component 10 (initially with reference to FIGS. 1-4) that is included in valves in accordance with the invention. Other possible components of a complete valve may be mentioned in this discussion of component 10, but more attention will be given to such possible other components later in this specification. The valves of this invention are collapsible and expandable in the circumferential direction. FIGS. 1-4 and other early FIGS. show illustrative embodiments of these valves (or portions or components of these valves) in their circumferentially expanded condition configuration. Some of the later FIGS. illustrate how valves of this type circumferentially collapse. Alternative terms that may be used for circumferential (in the context of collapse and re-expansion of a valve) include annular (in the sense of ring-like (especially like a closed ring)), diametrical, radial, and the like.

The valves of this invention can be used in patients who need an aortic valve replacement, but who may not be treated adequately by currently available prostheses and/or procedures. Valves in accordance with this invention can be implanted percutaneously, transapically, or surgically, with or without resected and/or debrided native leaflets. Metal component 10 can be cut from a highly elastic and/or shape-memory alloy (e.g., nitinol) so that it is self-expanding, or from another metal (e.g., stainless steel, cobalt-chromium, platinum-iridium, etc.) that necessitates balloon expansion after annular reduction. A way that metal component 10 can be made is by using a laser to cut it from starting stock that is a metal tube. Alternatively, metal component 10 can be laser-cut from a flat metal sheet and then rolled into a hollow annulus in which the formerly free ends or side edges of the flat material are joined together by any suitable means such as welding.

Component 10 may have any or all of the features that are described in the following paragraphs.

Illustrative component 10 includes a collapsible and expandable "upper" ring portion 100, and a collapsible and expandable "lower" stent portion 200 (which is also a ring). (The words "upper" and "lower" are used only as convenient, relative terms, and without any intention to limit what is referenced to any particular orientation relative to some absolute reference direction). In general, the stent portion 200 surrounds the leaflets of the prosthetic valve. The blood inflow end or edge of the valve is at or adjacent the lower end or edge of stent portion 200 as viewed in FIG. 1. The blood outflow end or edge of the valve is at or adjacent the upper end of stent portion 200 as viewed in FIG. 1. Ring portion 100 is downstream from stent portion 200 in terms of the direction of blood flow through the valve. Moreover, the annular structure of ring portion 100 is preferably downstream from the reach of any portion of the leaflets of the valve in any operating position of these leaflets so that no portion of the leaflets can ever contact any significant portion of at least the annular structure of ring portion 100. Indeed, when the valve is in use in a patient, ring portion 100 is typically disposed in the patient's aorta downstream from the valsalva sinus.

Ring portion 100 and stent portion 200 both include a number of cells (each of which has a closed perimeter surrounding an open center) that are collapsible and expandable in a direction that is circumferential around component 10. Reference number 110 points to a typical such cell in ring portion 100, and reference number 210 points to a typical such cell in stent portion 200. Making component 10 of such cells contributes to the ability of component 10 to shrink (collapse) and/or expand in the circumferential direction. Ring portion 100 may have cells of different sizes than the cells of stent portion 200 in order to facilitate ring portion 100 reaching a different, finally expanded diameter than stent portion 200. For example, it may be desirable for ring portion 100 to reach a final expanded diameter that is greater than the final expanded diameter of stent portion 200. This may enable ring portion 100 to better fill and bear against the adjacent portion of a patient's aorta (e.g., at or near the sinotubular junction (where the aortic sinus bulge ends and the aorta begins)), while stent portion only has to fill and bear against the patient's diametrically smaller aortic valve annulus. Cells 110 in ring portion 100 that are larger than cells 210 in stent portion 200 may help ring portion 100 expand to the above-mentioned larger final diameter.

Differential radial force may also be provided by ring portion 100 and stent portion 200. For example, it may be desirable for ring portion 100 to provide more radial force (to the adjacent aorta wall) than stent portion 200 provides (to the native aortic valve annulus). Larger cells (like 110) with "heavier" metal sides in ring portion 100 (as compared to stent portion 200) can contribute to causing ring portion 100 to apply more radially outward force than stent portion 200. A side of a cell that is "heavier" has a larger cross section (more material) than a cell side that is "lighter." Thus it will be noted that the sides of cell 110 are heavier (wider and/or thicker) than the sides of cell 210.

In general, the provision of ring portion 100 allows for greater overall structural integrity of component 10 (and hence the valve as a whole), while distributing holding forces more evenly. For example, this can avoid the need for a high-radial-force stent, which could cause undesirable deformation of the patient's mitral valve (which is adjacent to the aortic valve). This better, more widely distributed holding force can also reduce the need to use the patient's native, possibly stenotic leaflets (if present) as the primary anchoring mechanism for the prosthetic valve.

Illustrative component 10 includes barbs 120 that are placed on the distal (downstream) portion of the ring 100 that expands into the aorta. Barbs 120 (which point in the downstream direction) help prevent migration (especially downstream shifting) of the implanted valve. Other generally similar barbs can be employed at various other locations on component 10 to help prevent valve migration. For example, barbs can be provided that point upstream, downstream, clockwise, counter-clockwise, or in any other direction, and they can be provided on ring portion 100, stent portion 200, or both.

The lower (blood inflow edge) portion of stent portion 200 is designed to conform to the anatomy of the heart without impinging on the patient's mitral valve. In particular it will be noted that adjacent one of the three commissure posts or regions of component 10 (i.e., at reference 220a) the inflow edge of component 10 is higher than it is adjacent the other two commissure posts or regions (i.e., at references 220b and 220c). A valve including component 10 is preferably implanted so that higher inflow edge portion 220a is adjacent to the patient's mitral valve. This helps prevent the prosthetic valve from impinging on the mitral valve. This low profile of stent portion 200 means the area adjacent to the mitral valve is designed to reduce the possibility of chordal entanglement and mitral valve impingement. In general, the stent/valve is designed to reduce interference with various anatomical and/or physiological constraints. Such constraints may include avoidance of mitral valve impingement, avoidance of chordae entanglement, avoidance of interference with the heart's various electrical conduction system pathways, etc.

Dual open bars 130 are provided for connecting ring portion 100 to stent portion 200 in the vicinity of the tip of each commissure region of stent portion 200. This allows for redundant support in a high stress area, while also allowing some bending and/or twisting to conform to the patient's anatomy.

Stent portion 200 includes an independent stent-in-stent design as indicated at references 230a and 230b. In particular, stent portion 200 includes two congruent, serpentine, blood-outflow-edge-region members 230a and 230b. Each of these members 230 is a ring that extends annularly all the way around stent portion 200. Each of these members 230 undulates alternately up and down as one proceeds in the annular direction around the valve so that each member is "high" near the tip of each of three commissure regions 236 of the valve, and "low" between each annularly adjacent pair of such commissure regions. ("High" means extending farther in the blood flow direction; "low" means extending not as far in the blood flow direction. This undulation of members 230 may also be referred to as a serpentine pattern.) Everywhere in the annular direction around component 10 member 230b is higher than (i.e., spaced downstream from) member 230a. At several locations 232 that are spaced from one another annularly around component 10 connections or links are provided between members 230a and 230b. Elsewhere, however, members 230a and 230b are able to move relative to one another. Hence the description of this structure as an "independent stent-in-stent design."

This independent stent-in-stent design facilitates good leaflet coaptation near the top of each commissure post 236, while helping to maintain a flexible stent. This increased flexibility (which may contrast with designs that use a straight vertical bar for each commissure post region) may reduce stress concentration on the leaflets (which may be tissue, for example). Reduced leaflet stress concentration is conducive to longer valve life or durability. Amplifying what is being said about flexibility, making structure 230a relatively independent of structure 230b in the vicinity of stent posts 236 means that the stent posts (actually provided by structure 230a and not structure 230b) can be made as flexible as is desired. The relatively independent valve anchoring structure (e.g., ring 100, the lower portion of stent 200, and the structures 130 and 230b that link the two) can be made stiffer (relatively less flexible) for completely secure anchoring of the valve in the implant site.

Figure 3:
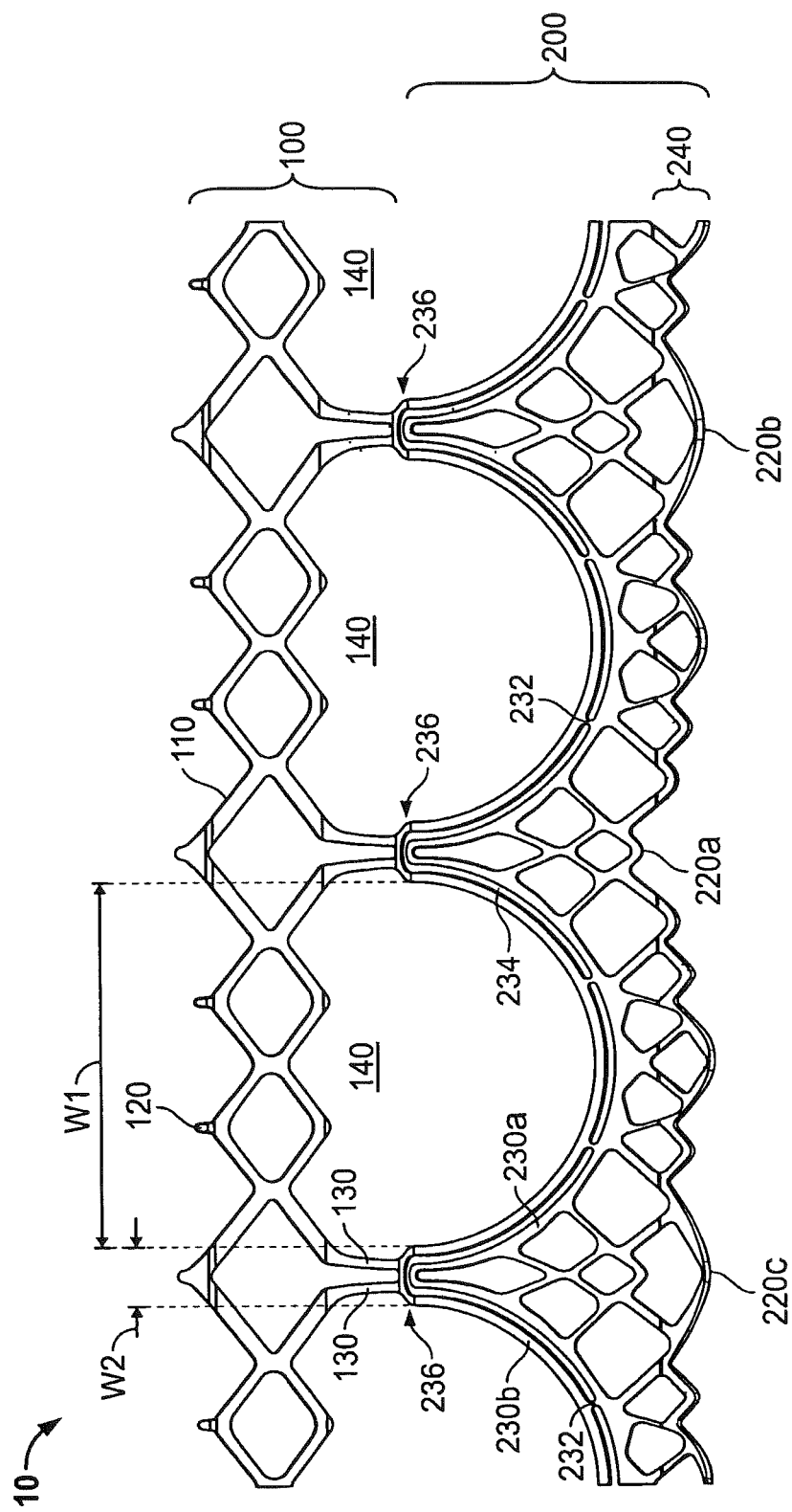
FIG. 3 shows the component of FIGS. 1 and 2 cut at one location around its perimeter and basically flattened out (although not all parts of the structure are shown lying in one plane such as the plane of the paper on which FIG. 3 is drawn).
Figure 4:
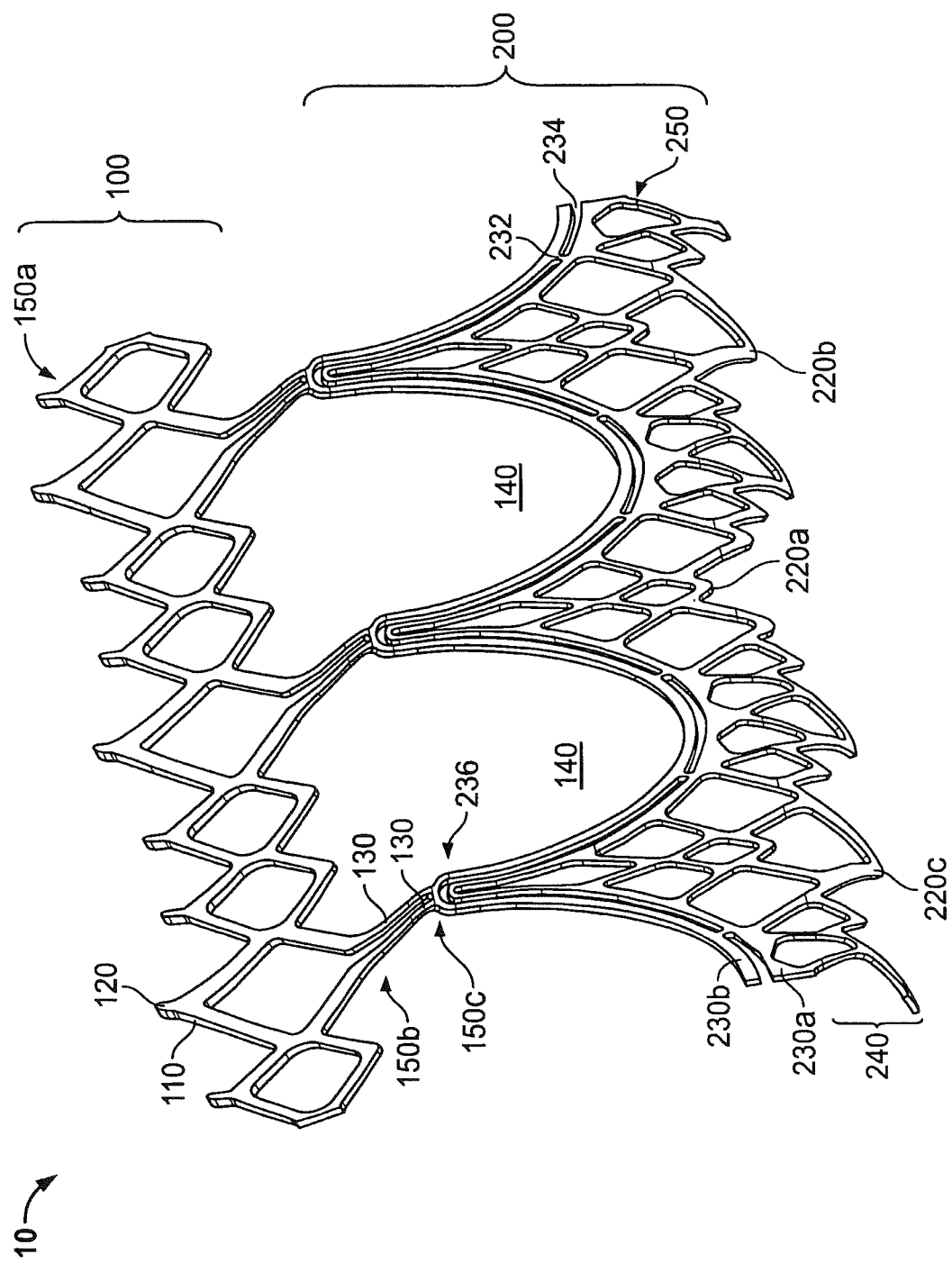
FIG. 4 is a simplified perspective or isometric view of what is shown in FIG. 3.

As shown in FIGS. 3 and 4, a lower "skirt" portion 240 of stent 200 and/or ring 100 can be deflected out of projections of the tubular geometric figure in which the major portion of stent 200 lies. In particular, these deflections may be radially outward from the above-mentioned tubular geometric figure projections. These radially outwardly projecting portions of component 10 (along with some radially outward force from the midsection of stent portion 200) help hold the implanted valve in place in the patient with or without the patient's native, stenotic leaflets to help hold it in place.

The smooth contours (in the annular direction) of the outflow edge 230a/230b of stent portion 200 may facilitate the use of naturally contoured leaflets. This may be unlike other designs that use a vertical bar for each commissure region. Additionally, this smooth outflow edge may help reduce or eliminate stagnant blood flow zones, which might otherwise arise where a leaflet abruptly changes direction at the bottom of a vertical bar. The above-mentioned smooth outflow edge contour is the result of outflow edge members 230a/230b being smoothly serpentine or undulating in the annular direction around structure 10.

Although component 10 includes a ring 100 in the patient's aorta, there are large openings 140 between stent portion 200 and ring portion 100 to allow for blood flow to freely pass to the coronary arteries. These large openings 140 also reduce the chance of leaflet abrasion from the free edge due to leaflet contact with other parts of the prosthetic valve structure.

As has been mentioned, different cell dimensions in different parts of component 10 allow for different amounts of expansion and force generation in different parts of the device. Some of this cell structure can be converted to other circumferentially expandable structure (e.g., serpentine or undulating members extending generally in the circumferential direction) to allow for different types of behavior (e.g., with respect to amount of expansion and/or amount of force that can be generated).

To further reduce or eliminate leaflet abrasion at the leaflet attachment site, stent portion 200 can first be covered with fabric, followed by a thin layer of buffering tissue, and finally leaflet tissue. Inventive aspects of this kind will be discussed in more detail later in this specification.

The elongated slots 234 between the two blood-outflow-edge-region members 230a and 230b allow for (1) a flexible stent (as discussed earlier in this specification), (2) uninterrupted suturing of other materials such as leaflets over structure 10 (as opposed to smaller stent holes hidden beneath those other materials), (3) easily polished edges, and (4) a reduction in stress concentration from point suturing.

Skirt portion 240 can be scalloped (e.g., higher and less radially deflected in area 220a than elsewhere around structure 10). This can allow skirt 240 to conform more readily to the natural contours of the patient's aortic annulus, which may improve the placement and holding force of the prosthetic valve, as well as helping to reduce or eliminate paravalvular leakage.

Bends in certain areas like 150a, 150b, 150c, and 250 can result in component 10 having different diameters at different points along its length. ("Length" refers to distance or location along the axis of blood flow through the device. A "bend" is typically a deflection about a geometric circumference of the device. FIG. 4 shows what will be the inner surface of component 10 in a finished valve. The outer surface of component 10 is not visible in FIG. 4.) Again, different diameters of component 10 at different locations along the length of that component allow the valve to better conform to adjacent structures in the patient's anatomy (e.g., the aorta toward the upper end of component 10, or the sub-annular geometry toward the lower end of component 10).

By conforming to the portion of the heart below the aortic valve, the holding force and paravalvular seal is improved.

The upper portion of the stent-in-stent design (e.g., in areas like those referenced 236 and 130) can be contoured to the shape of the patient's native aortic root. By this it is meant that these upper portions of the stent-in-stent design can gradually taper outward with the aorta since the aorta is larger than the native valve annulus. This can provide additional anchoring of the prosthetic valve to the patient's anatomy.

Another possibility is to have this portion (e.g., upper serpentine member 230b) bend away (i.e., radially outwardly) from other adjacent portions of the valve) to more gradually slope to the aorta diameter. This can allow for this section to be completely out of the way of the leaflet tissue attachments or free edges.

Component 10 can be partially or completely covered in one or more layers of material or combinations of materials (e.g., polyester, tissue, etc.). This layer or layers can allow for such things as better tissue in-growth, abrasion protection, sealing, and protection from metal leachables such as nickel from nitinol. Again, various aspects of how component 10 can be covered will be considered in more detail later in this specification.

Figure 5:
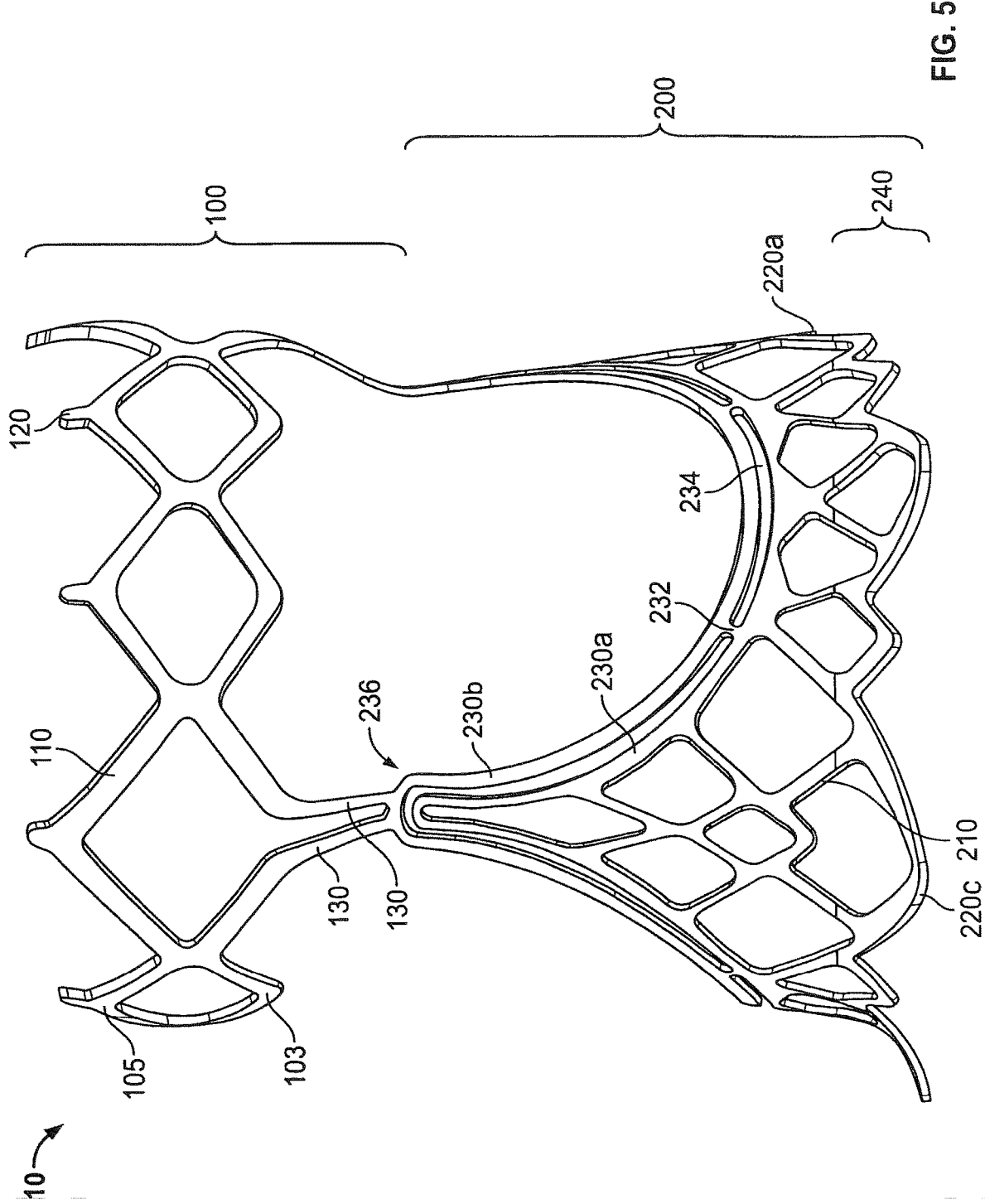
FIG. 5 is a simplified, partial, elevational view of a component that is at least generally similar to what is shown in FIG. 1.

FIG. 5 shows a side view of an embodiment of component 10 in which the radial shaping is more fully developed and depicted in at least some of the various ways that are shown and described earlier in this specification. FIG. 5 shows only one side (approximately half) of component 10. The opposite side (i.e., the rear half) is omitted from FIG. 5 for greater clarity. It will be noted that component 10 in FIG. 5 has different diameters at different points along its length. (Diameters are horizontal in FIG. 5. Length is vertical in FIG. 5 (parallel to the axis of blood flow through a finished and implanted valve).) Diameter changes in FIG. 5 tend to be relatively smooth. Even the rate of diameter change tends to be relatively smooth (not too abrupt at any point along the length of the device) throughout component 10 in FIG. 5. Note again the base skirt flare 240 and the expanded section 100 for the aorta in FIG. 5. As mentioned earlier, the base flare helps to secure the valve in place, and also to direct blood flow and prevent leakage around the outside of the valve (paravalvular leakage). Another possible feature that is shown in FIG. 5 (and carried through into some subsequent FIGS. like FIGS. 8 and 9) is contouring or curving of aortic ring 100 radially inwardly at the tips (i.e., at both the lower (upstream) tips like 103 and the upper (downstream) tips like 105). This can help reduce or avoid perforation and/or dissection of the aorta by ring portion 100. The embodiment of component 10 that is shown in FIG. 5 is used as the component 10 in the series of FIGS. that will be discussed next.

Figure 6:
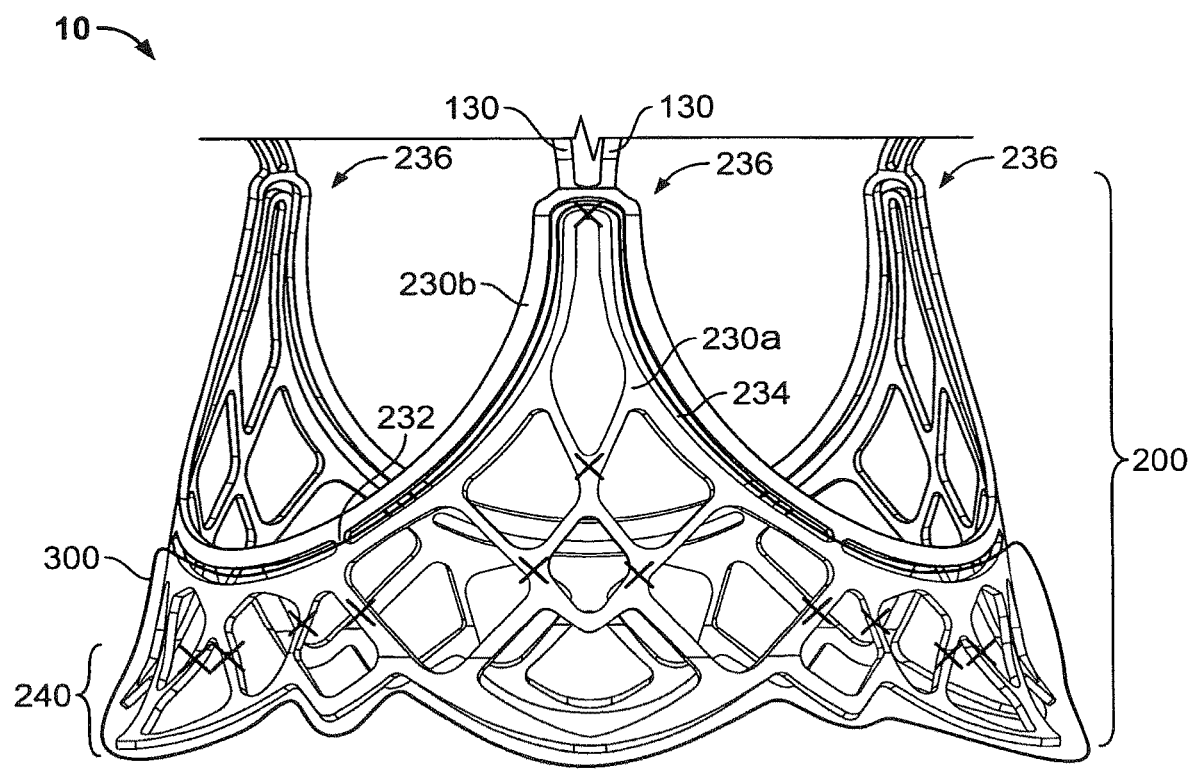
FIG. 6 is similar to a lower portion of FIG. 5, but with the full annular structure shown, and with the addition of another component also shown.

FIG. 6 illustrates a possible first step in attachment of other material to component 10. FIG. 6 and subsequent FIGS. tend to show the added material as though it were transparent (which, in fact, it typically is not). Thus these FIGS. tend to show the added material, for the most part, by means of a line at the visible limits of the material. In addition, some of these FIGS. show only the material being added in the step that is the subject of that FIG. Such a FIG. tends to omit depiction of material that was added in an earlier step or steps. The earlier-added material is still present, but it is not specifically depicted so that the FIG. that omits its depiction can focus on the material currently being added.

Continuing specifically with FIG. 6 (which shows only stent portion 200 and omits depiction of ring portion 100), this FIG. shows covering all of stent portion 200 below member 230b with a layer of material 300 such as fabric. This covering may be both inside and outside the covered portion of component 10. Among the possible purposes of material 300 may be (1) promotion of tissue in-growth, (2) blood flow/sealing, and (3) to provide an attachment base for subsequent layers of material. All material (i.e., 300 and subsequent material(s)) can be attached to component 10 by means of suturing around component 10 struts and/or through dedicated eyelets and slots (not shown) in component 10. The "X" marks in FIG. 5 indicate some possible locations for such sutures. Examples of fabrics that are suitable for material 300 include Dacron, polyester, and Teflon.

Figure 7:
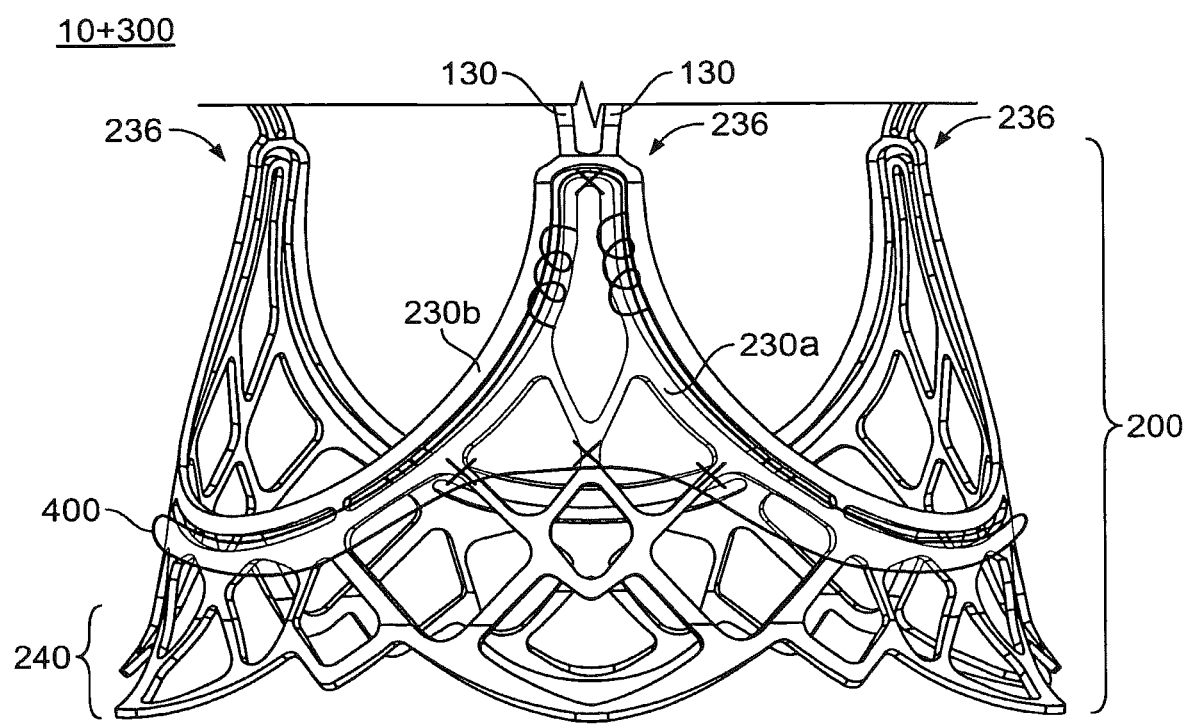
FIG. 7 is similar to FIG. 6, but with another additional component shown.

FIG. 7 shows the addition of more material 400 over a portion of material 300. (Again, as explained earlier, FIG. 7 omits depiction of material 300 (which is still present on component 10) so that all attention can now be given to material 400. FIG. 7 also omits depiction of upper ring portion 100.) In particular, material 400 is applied over the upper portion of material 300, both inside and outside the structure being built up. Material 400 may be a lubricious covering such as tissue (e.g., pericardium from any of several species, submucosa, and/or peritoneum) or polymer for sealing, reduced leachables, and a buffer between the stent and the moving leaflets. Again, the "X" marks, and now also the spiral marks, indicate some examples of where material 400 may be sutured to the underlying structure.

Figure 8:
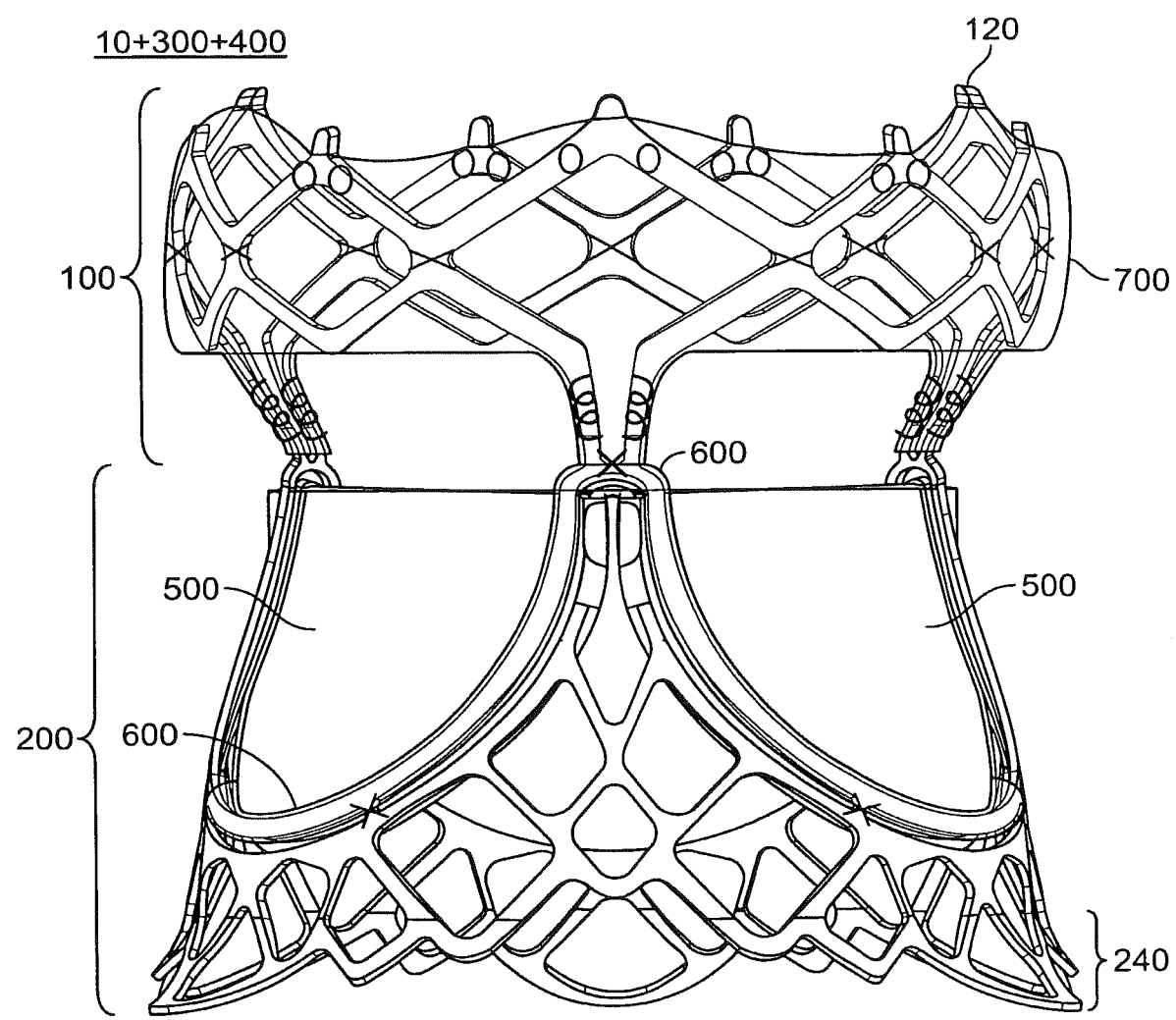
FIG. 8 is again similar to FIG. 5, but with the full annular structure and still more added components shown.

FIG. 8 illustrates addition of final material and leaflets to the structure being built up as described in the preceding paragraphs. A sheet of leaflet material 500 is added between each annularly adjacent pair of commissure regions. The U-shaped "lower" edge of each such sheet of leaflet material can be passed through the slots 234 between members 230a and 230b and sutured to the underlying structure. The "upper" edge of each such leaflet sheet is the "free" edge of that leaflet. Each leaflet sheet is shaped and includes sufficient material between the commissure regions to which it is attached as described above so that the free edges of the three leaflets can come together in the interior of the valve and thereby close the valve to prevent reverse blood flow through the valve when it is implanted and in use in a patient.

Typically after leaflets 500 have been added to the structure being built up, a lubricious covering 600 (e.g., porcine pericardium or polymer) may be added over member 230b. Covering 600 may also cover the lower portions of struts 130. (FIG. 8 shows covering 600 on the foreground portions of the valve, but omits depiction of it toward the rear to avoid over-complicating the drawing.) Covering 600 prevents leachables and reduces any leaflet abrasion.

In addition to elements 500 and 600, FIG. 8 shows that material 700 (e.g., a fabric such as Dacron, polyester, or Teflon) may or may not be provided to surround the section of component 10 that will be in contact with the aorta when the valve is in use in a patient. If provided, such material 700 can reduce leaching of metal and can help to secure the valve in place via tissue in-growth. Note that if barbs 120 are present on structure 10, they may remain uncovered for embedding into the patient's tissue.

Figure 9:
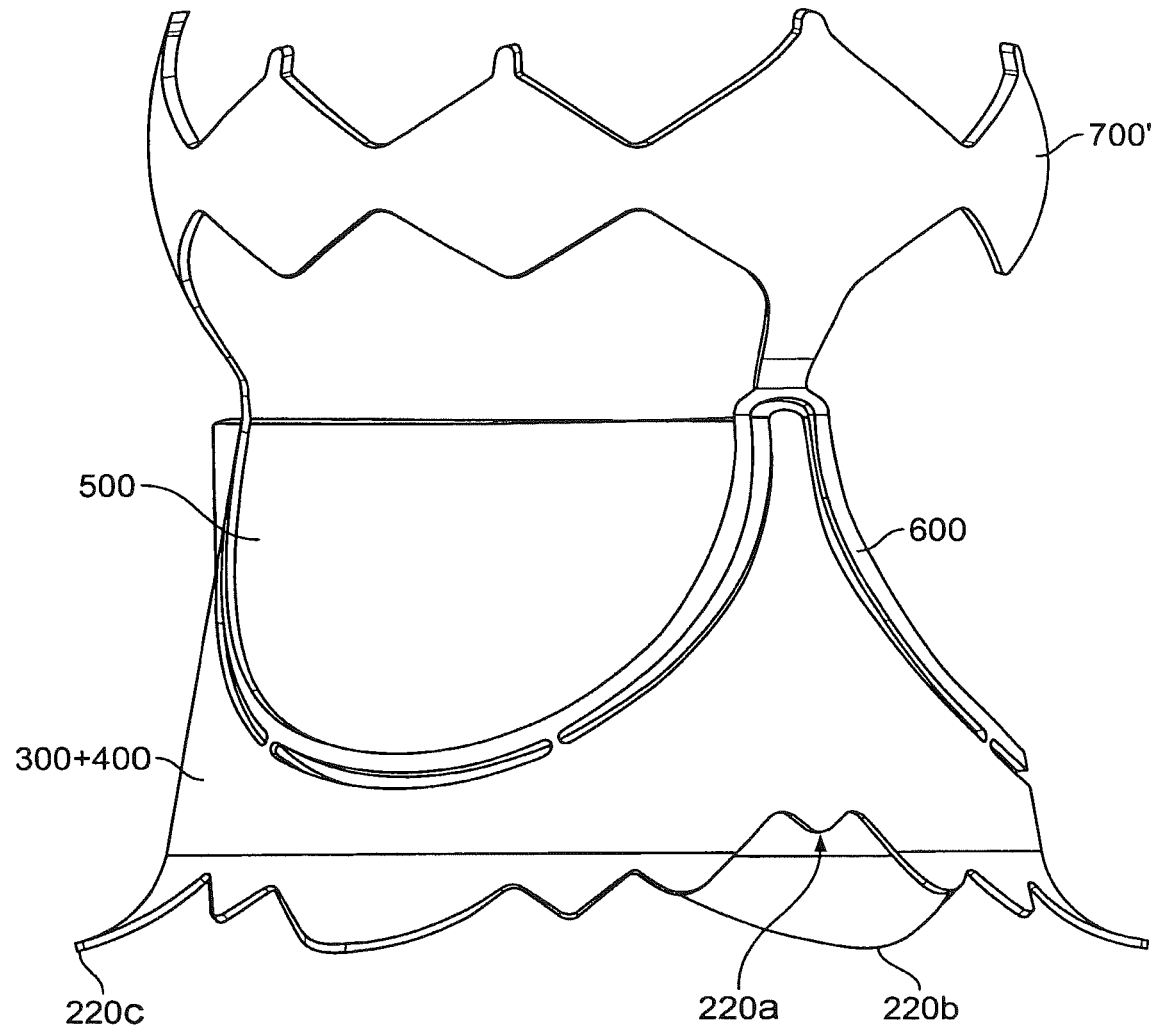
FIG. 9 is a simplified elevational view of an illustrative embodiment of a complete prosthetic heart valve in accordance with the invention.

FIG. 9 shows another illustrative embodiment of a finished valve. The only significant difference from FIG. 8 is that in FIG. 9 material 700' covers the barbs 120 at the top of the valve. Note that the close suturing of the various material layers to the underlying structure leaves the perimeter limits or contours defined by component 10 as substantially the same perimeter limits or contours of the finished valve. As just one example of this, the scalloping of the lower portion of component 10 (e.g., at 220a), which is provided to avoid impinging on the patient's mitral valve, remains a feature of the finished valve.

By way of recapitulation and further amplification of the above, some refinement of the terminology used in the foregoing may be helpful to better distinguish the present invention from previously known structures. FIG. 10 shows again a portion of the primary metal component 10 that has been shown in some of the earlier FIGS. A portion of FIG. 10 has been shaded to emphasize the location of a flexible strut structure 280 that connects ring portion 100 to stent portion 200. Strut structure 280 is one of three similar strut structures that are spaced from one another annularly around component 10. Each strut structure 280 is located adjacent a respective one of the three commissure regions 236 of the valve. Ring portion 100 and stent portion 200 are connected to one another substantially only by strut structures 280. Because each of these strut structures is adjacent a respective one of commissure regions 236, and because there is no other connecting structure between ring portion 100 and stent portion 200, component 10 defines a relatively large and unobstructed opening 140 between each annularly adjacent pair of commissure regions 236. This helps a valve of this invention avoid occluding the ostia of the coronary arteries. These ostia can connect to the aorta where component 10 provides large and unobstructed openings 140.

Figure 10:
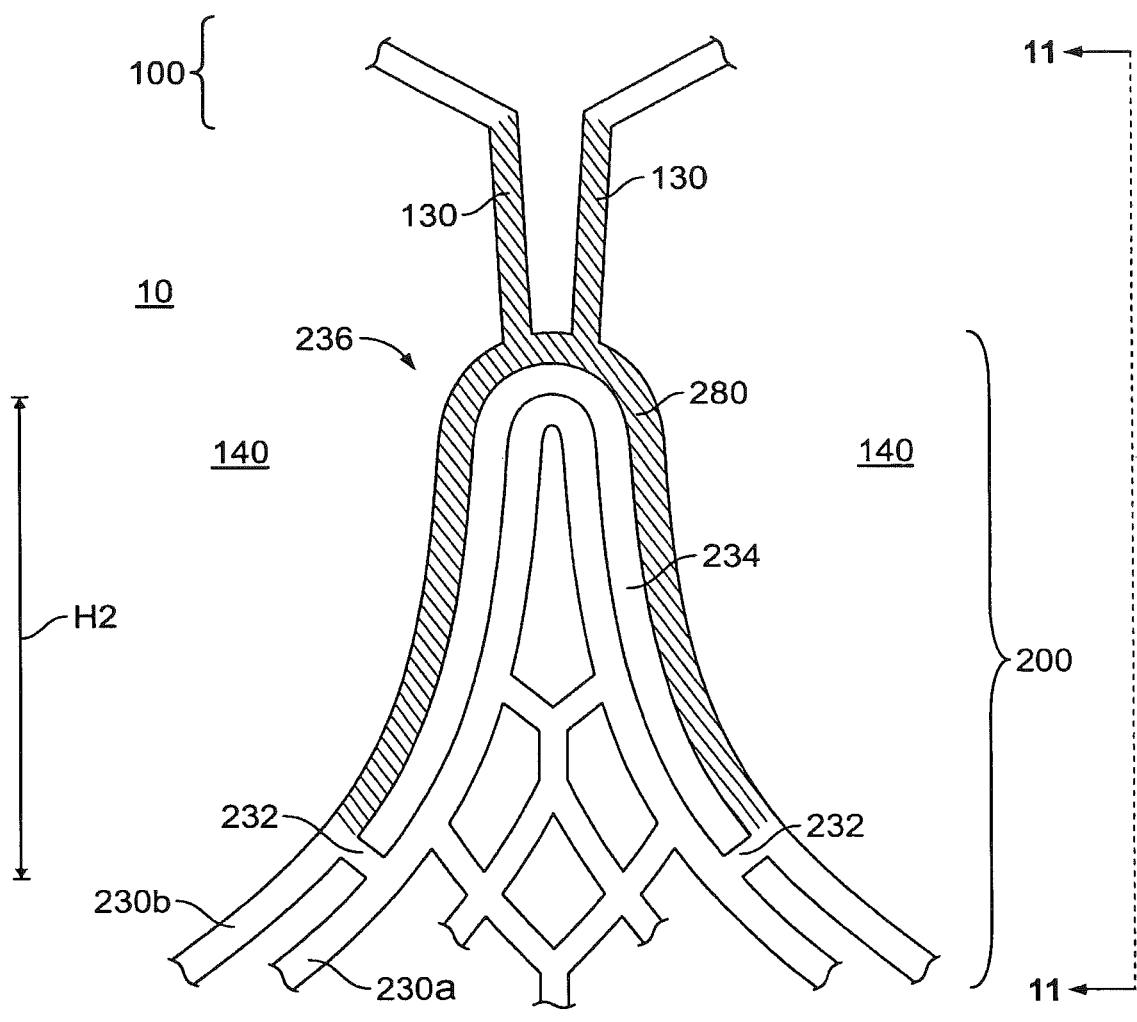
FIG. 10 shows a representative portion of a structure like that shown in several earlier FIGS., with certain parts emphasized with special shading for purposes of further discussion.

In the illustrative embodiment shown in FIG. 10, representative strut structure 280 (shaded for emphasis) effectively begins (toward the bottom) where member 230b is last connected to the remainder of stent portion 200 in the blood flow direction. This is at the uppermost links 232 that are shown in FIG. 10. Strut structure 280 then includes the portion of member 230b that is above these uppermost links 232. Strut structure 280 also includes dual open bars 130. At its upper end strut structure 280 ends where bars 130 merge into the annular structure of ring portion 100.

From the foregoing it will be seen that strut structure 280 connects to the remainder of stent portion 200 only well below the upper, free-end tips of the associated commissure region 236. (In FIG. 10 the arrow from reference number 236 points to the tip of that commissure region.) In other words, the uppermost points of attachment 232 of strut structure 280 to the remainder of stent portion 200 are at a significant distance below the tip of the associated commissure region 236. For example, if the distance from the lowest to the highest point along the undulation of member 230a around component 10 is H1 (see FIG. 1), and if the distance from the highest link 232 (between members 230b and 230a) to the tip 236 of the adjacent commissure region is H2 (see FIG. 10), then H2 is preferably about 50% or an even larger percentage of H1. Still more preferably, H2 is about 75% or an even larger percentage of H1. (FIGS. 1 and 10 are not, of course, drawn on the same scale.) In other words, strut structure 280 extends down along at least about 50% (more preferably at least about 75%) of the height of the associated commissure "post" portion of component 10 to its points 232 of attachment to the remainder of stent portion 200. In the annular direction this downwardly extending portion of strut structure 280 preferably closely follows the associated commissure post (actually provided by member 230a) to avoid encroaching significantly on the desirable large open spaces 140 between annularly adjacent commissure regions 236.

Figure 11:
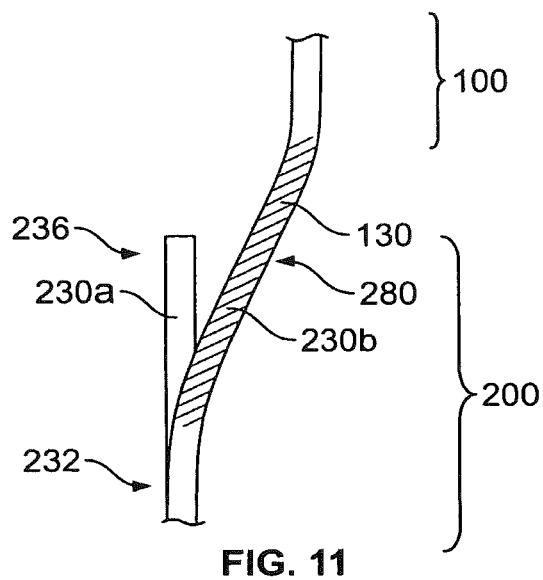
FIG. 11 is a simplified depiction of what is shown in FIG. 10 from the direction indicated by the arrows 11-11 in FIG. 10.

FIG. 11 is a view taken from the side of FIG. 10 as indicated by the line 11-11 in FIG. 10. FIG. 11 again shows representative strut structure 280 shaded for emphasis. FIG. 11 shows that strut structure 280 can be deflected radially out from the tubular geometric shape in which the remainder of stent portion 200 tends to lie (in this extremely simplified depiction). This radial outward deflection of strut structure 280 can begin just above uppermost links 232, which (as has been mentioned) can be quite low relative to where the tips 236 of the commissure posts are. All of this can help keep strut structure 280 away from contact with any moving portions of the valve leaflets (anchored, in the vicinity of what is shown in FIG. 11, to member 230a and not to any portion of structure 280) when the valve is in use in a patient. It can also facilitate making a gradual transition from the smaller circumferential size of the remainder of stent portion 200 to the larger circumferential size of ring portion 100. FIG. 11 illustrates the relative independence of strut structure 280 downstream from its downstream-most connection points 232 to the remainder of stent portion 200. This independence of strut structures 280 and the adjacent portions of the remainder of stent portion 200 (e.g., the adjacent portion of member 230a) allows these features to be shaped, to deflect, and/or to flex independently of one another (e.g., in the radial direction). Leaflets 500 and other materials 300, 400, 600, and 700 are preferably added and attached in such a way as to not significantly interfere with this independence of strut structures 280 and the adjacent parts of the remainder of stent portion 200. In other words, leaflet and other materials and their associated attachment sutures preferably do not span between strut structures 280 and adjacent parts of stent portion 200 in a way that would tie these otherwise independent features together with undue relative-motion constraint. For example, in the vicinity of what is shown in FIG. 11, leaflet material preferably ends at member 230a (extending only to the left from the portion of member 230a that is shown in FIG. 11). Leaflet material preferably does not extend significantly to the right from member 230a and is preferably not attached to structure 280 per se.

Figure 12:
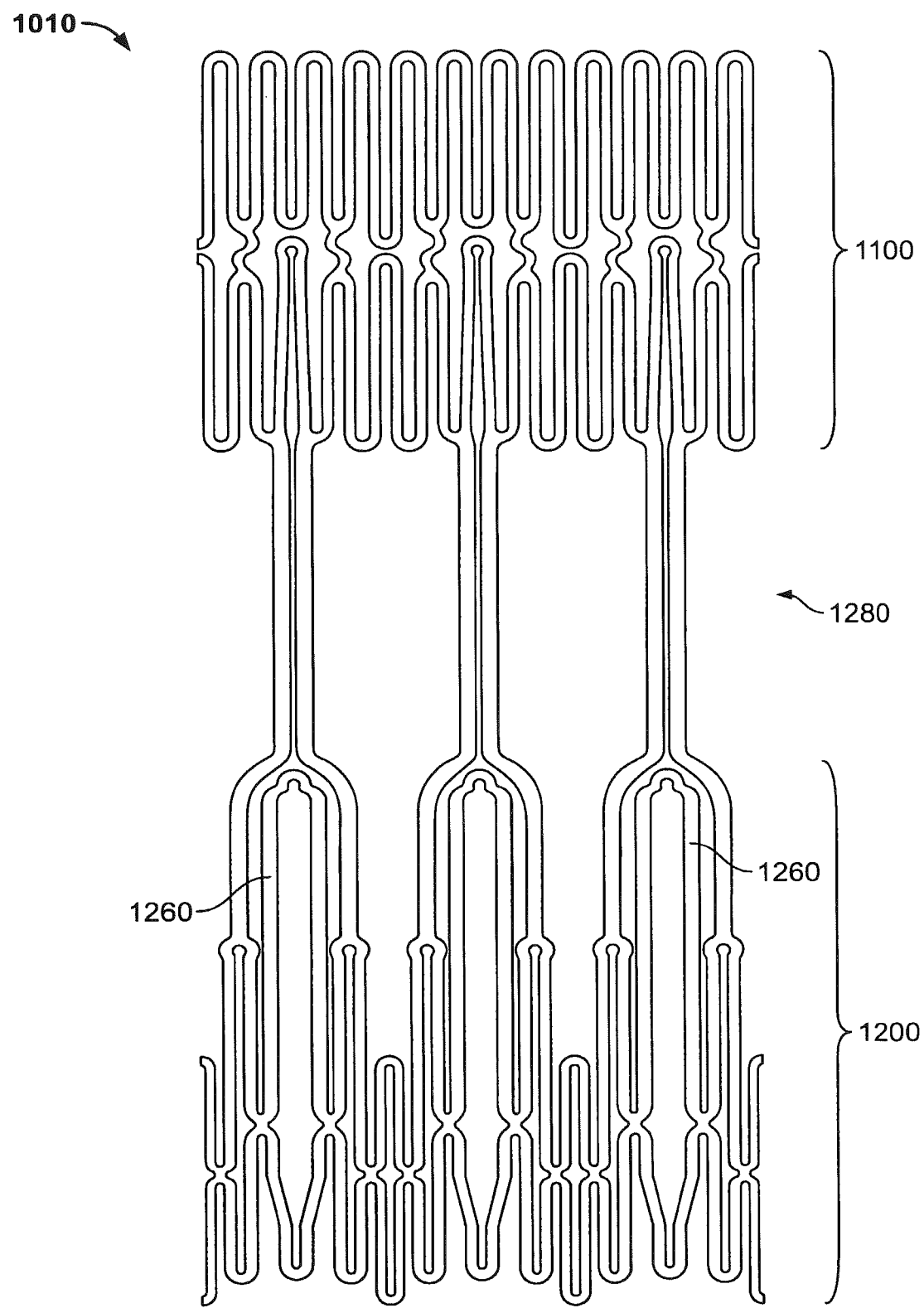
FIG. 12 is similar to FIG. 3, but for another illustrative embodiment in accordance with the invention and in another operating condition.
Figure 13:
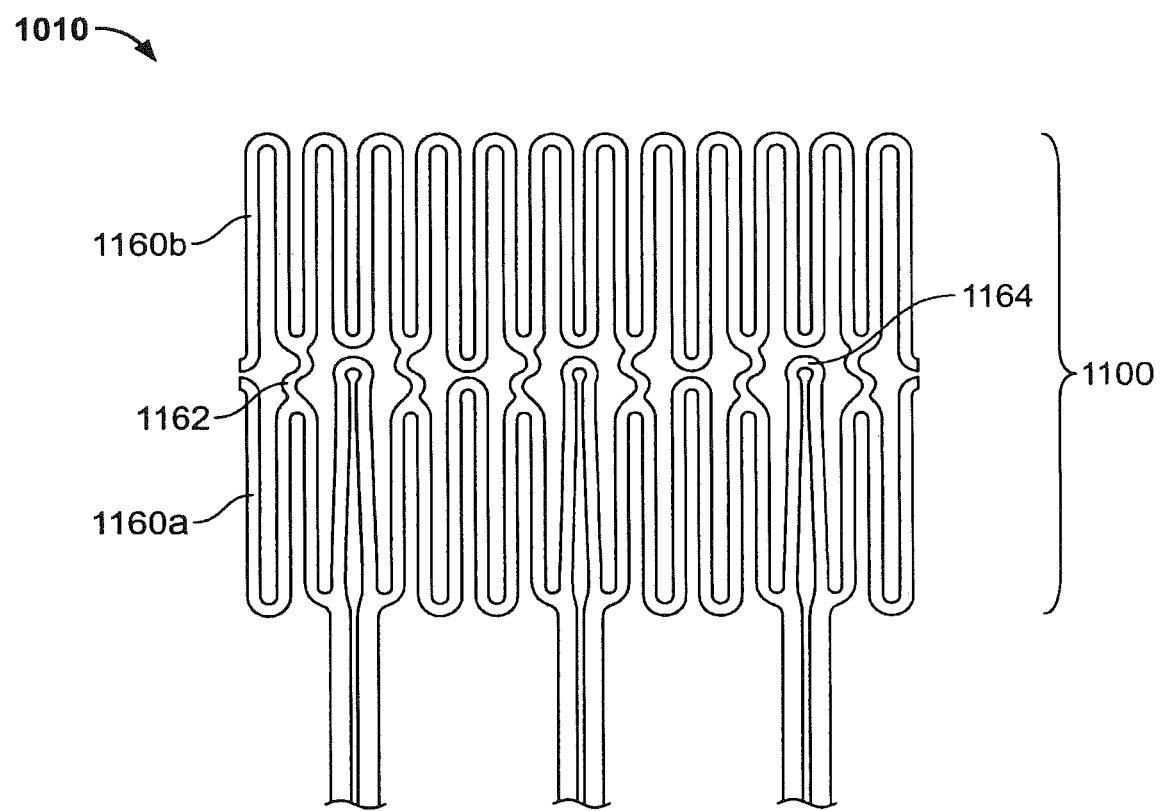
FIG. 13 is an enlargement of a portion of FIG. 12.
Figure 14:
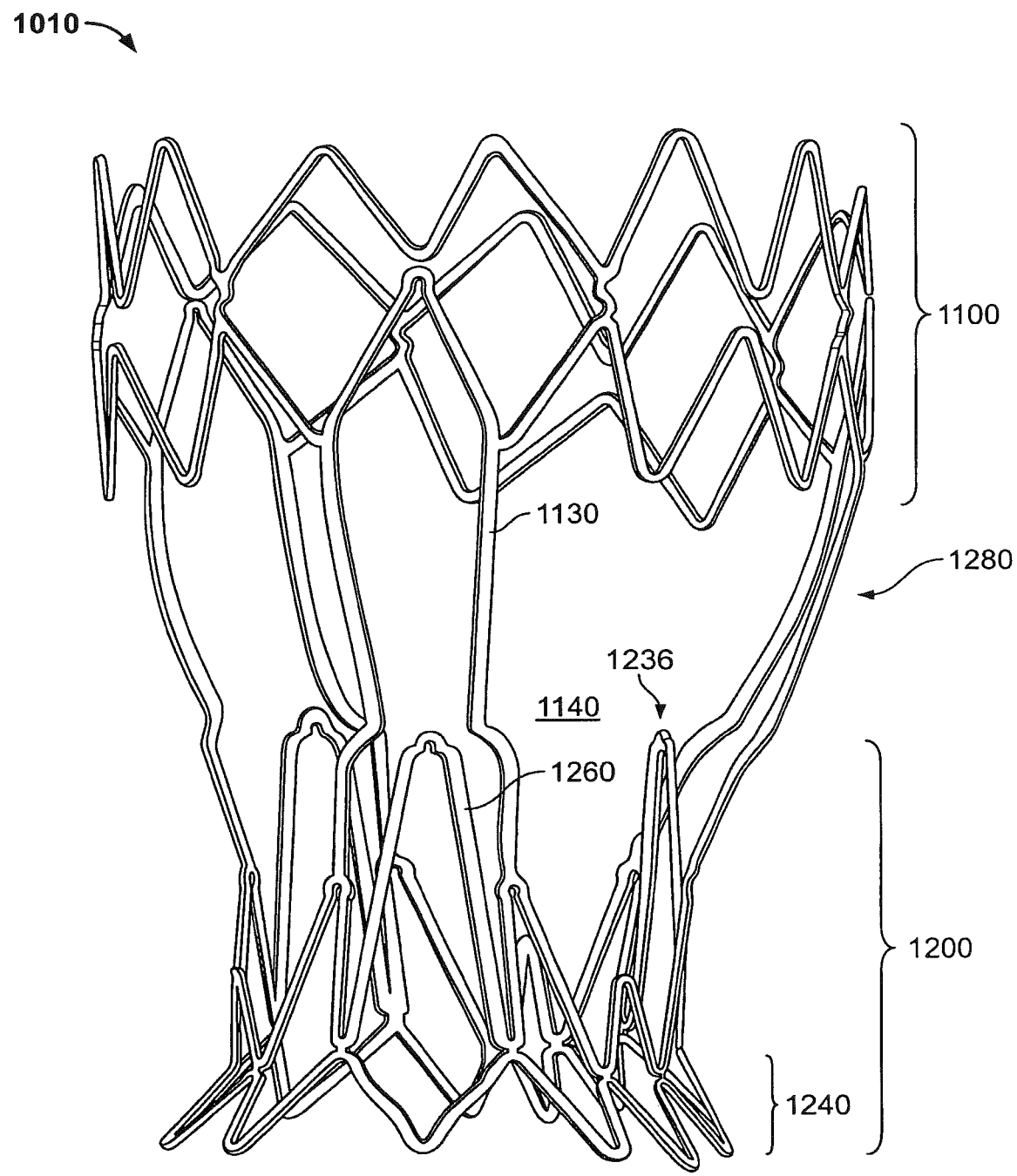
FIG. 14 shows the FIG. 12 structure in the round and fully expanded.

FIGS. 12-14 show the primary (tubular or hollow cylindrical) metal component 1010 of another illustrative embodiment of a prosthetic heart valve in accordance with this invention. Elements in FIGS. 12-14 that are generally similar to previously described elements have reference numbers in FIGS. 12-14 that are increased by 1000 from the reference numbers previously used for the similar elements. FIG. 12 shows component 1010 cut axially along its length and then flattened (this is done solely to simplify the depiction), but in the left-to-right condition that it has when it is annularly compressed or collapsed. FIG. 13 shows an enlargement of the upper portion of FIG. 12. FIG. 14 shows component 1010 in the round and in its fully expanded state.

In the embodiment shown in FIGS. 12-14 the leaflets of the valve can be attached to the angled posts 1260. In this embodiment the aorta portion 1100 is made up, for the most part, of primary serpentine members 1160a and 1160b. Each of these members undulates in the axial direction (parallel to the axis of blood flow through the finished and implanted valve) as one proceeds annularly around the valve. In addition, secondary serpentine members 1162 are used to connect members 1160a and 1160b to one another. Secondary serpentine members 1162 undulate in the annular direction as they proceed generally axially between members 1160a and 1160b. The use of serpentine members 1160 and 1162 in aorta portion 1100 allows for greater flexion and/or extension. For example, this can aid in the flexibility of component 1010 within a catheter bending along a tortuous path. It can allow for conformance to bending when placed in the ascending aorta where it begins to arch. It can also compensate for pulsatile expansion/contraction of the aorta. Stress relieving features 1164 aid in flexibility and reduction in stress.

As a general matter, embodiments like those shown in FIGS. 12-14 and in subsequent FIGS. may be capable of collapsing to a smaller circumferential size than embodiments like those shown in FIGS. 1-11. Thus, for example, any of the embodiments shown herein may be suitable for delivery (in a collapsed condition) into the patient through a small incision and, e.g., through the apex of the heart. Embodiments like those shown in FIGS. 12-14 and subsequent FIGS. may be additionally suitable for delivery in other ways requiring collapse of the valve to an even smaller circumferential size. An example of such other delivery is through the femoral artery.

Figure 15:
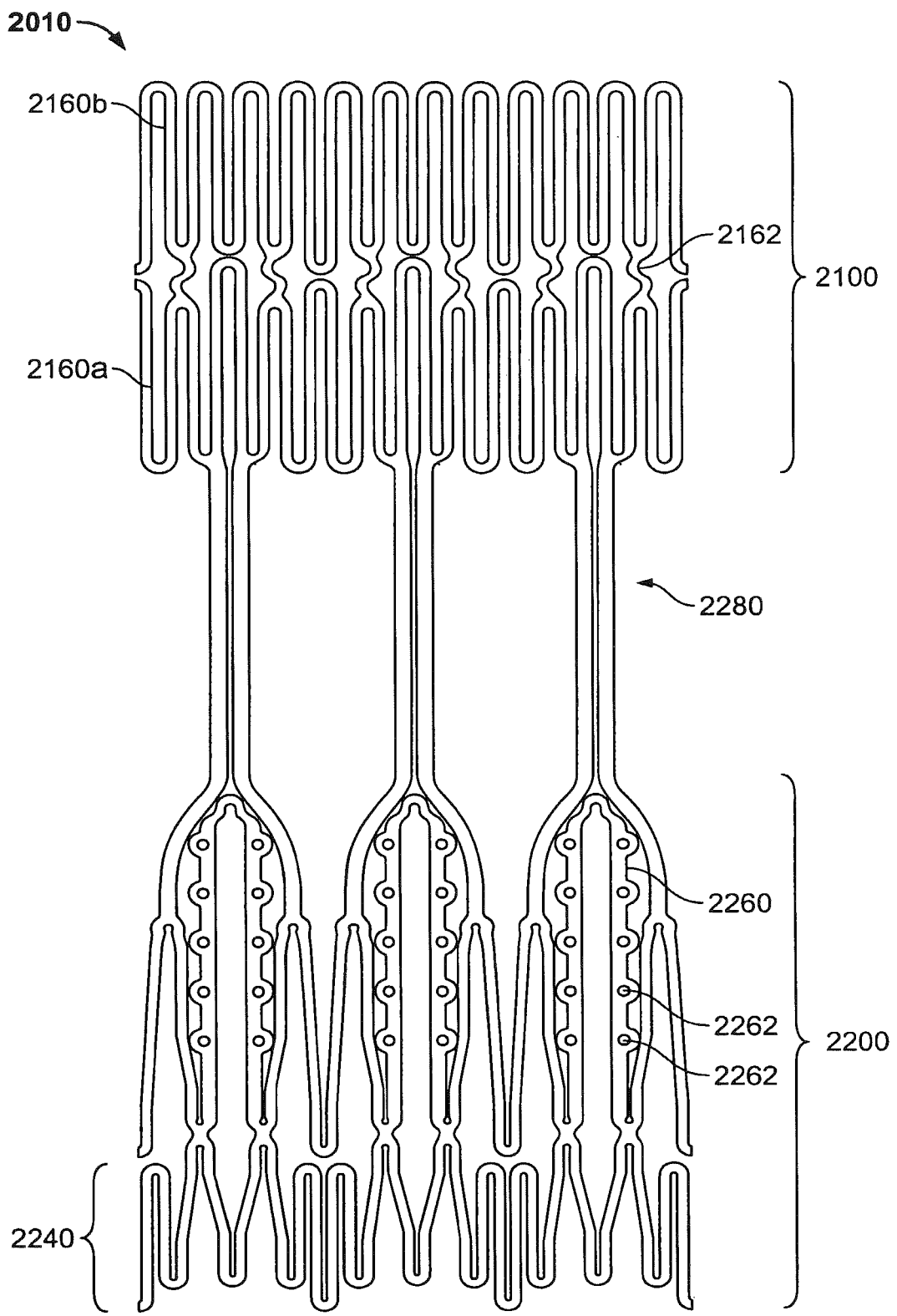
FIG. 15 is similar to FIG. 12 for yet another illustrative embodiment of the invention.
Figure 16:
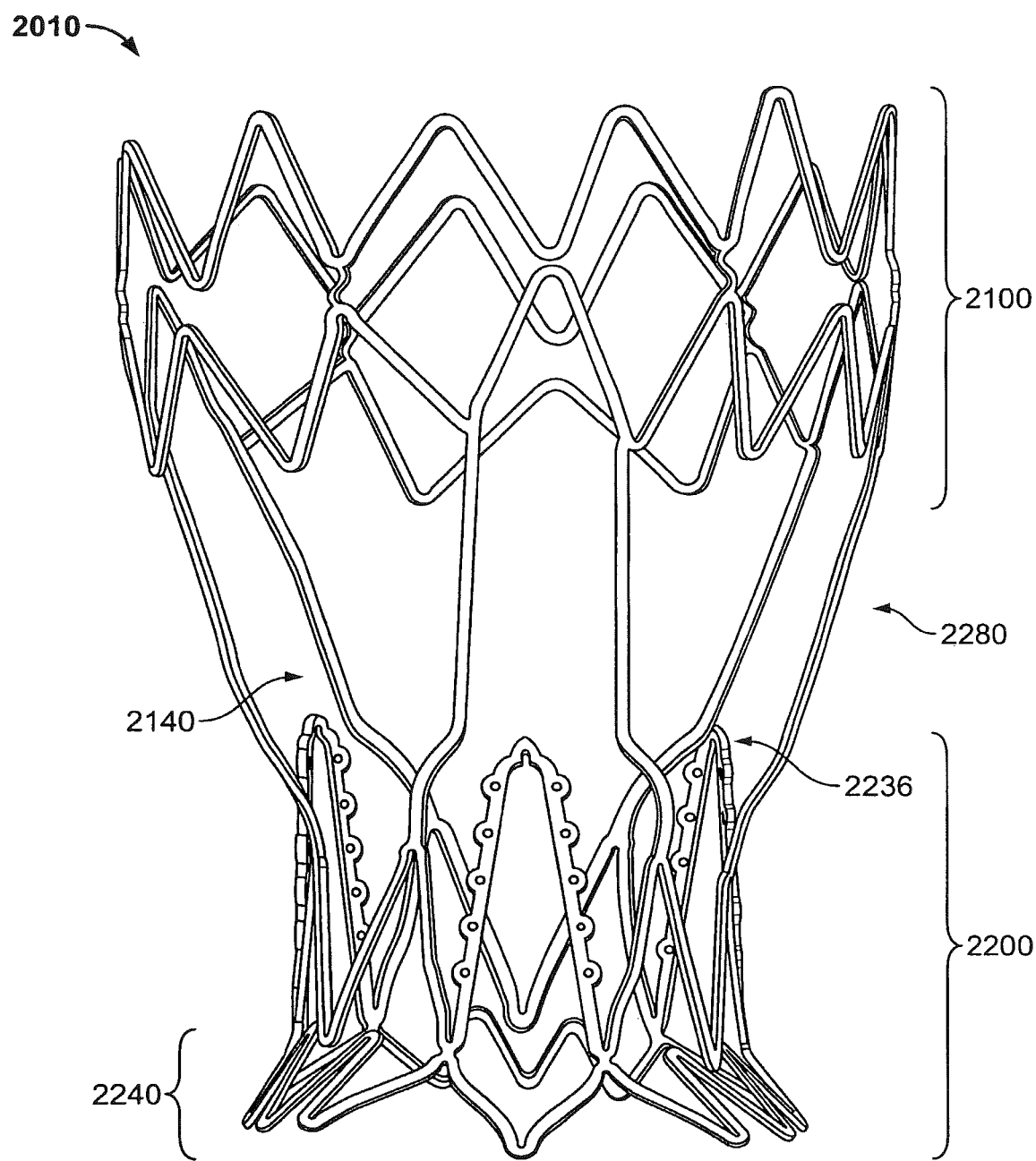
FIG. 16 is similar to FIG. 14, but for the FIG. 15 embodiment.

FIGS. 15 and 16 show the primary (tubular or hollow cylindrical) metal component 2010 of yet another illustrative embodiment of a prosthetic heart valve in accordance with the invention. Elements in FIGS. 15 and 16 that are generally similar to previously described elements have reference numbers in FIGS. 15 and 16 that are increased by 1000 or 2000 from the reference numbers previously used for the similar elements. To simplify the depiction, FIG. 15 shows component 2010 cut axially along its length and then flattened, but otherwise in the condition that it has when it is annularly compressed or collapsed. FIG. 16 shows component 2010 in the round and in its fully expanded state. Like the embodiment shown in FIGS. 12-14, the FIGS. 15-16 design allows for leaflet attachment to angled posts 2260, but the FIGS. 15-16 design also has a set of apertures 2262 to aid in suturing (e.g., for attachment of the leaflets.) Although shown as round or eyelet-shaped in FIGS. 15 and 16, apertures 2262 (or similar apertures in any other embodiment) can have any other shape, if desired. Slots are just one example of such other possible shapes for these apertures.

Figure 17:
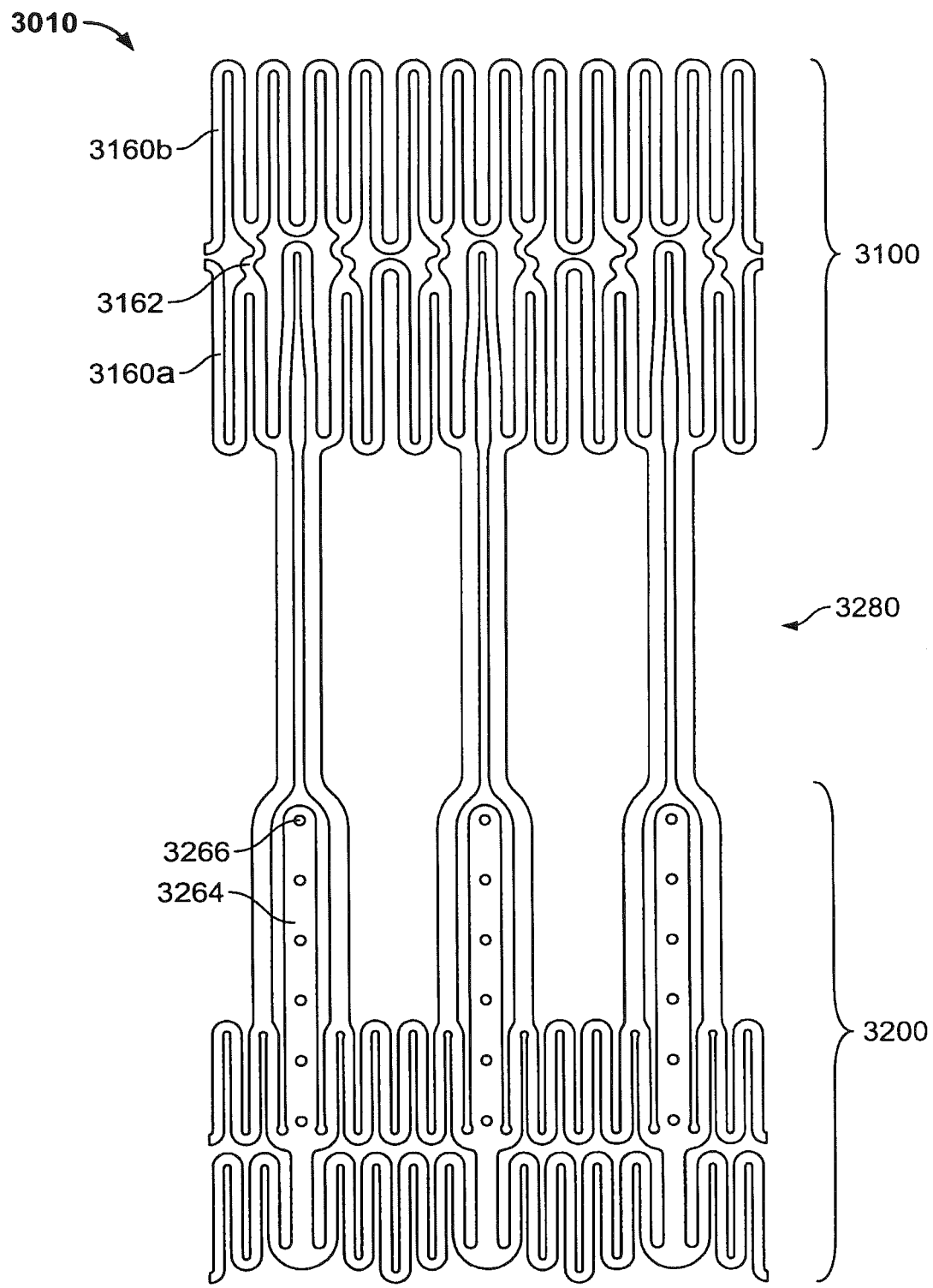
FIG. 17 is similar to FIG. 15 for still another illustrative embodiment of the invention.
Figure 18:
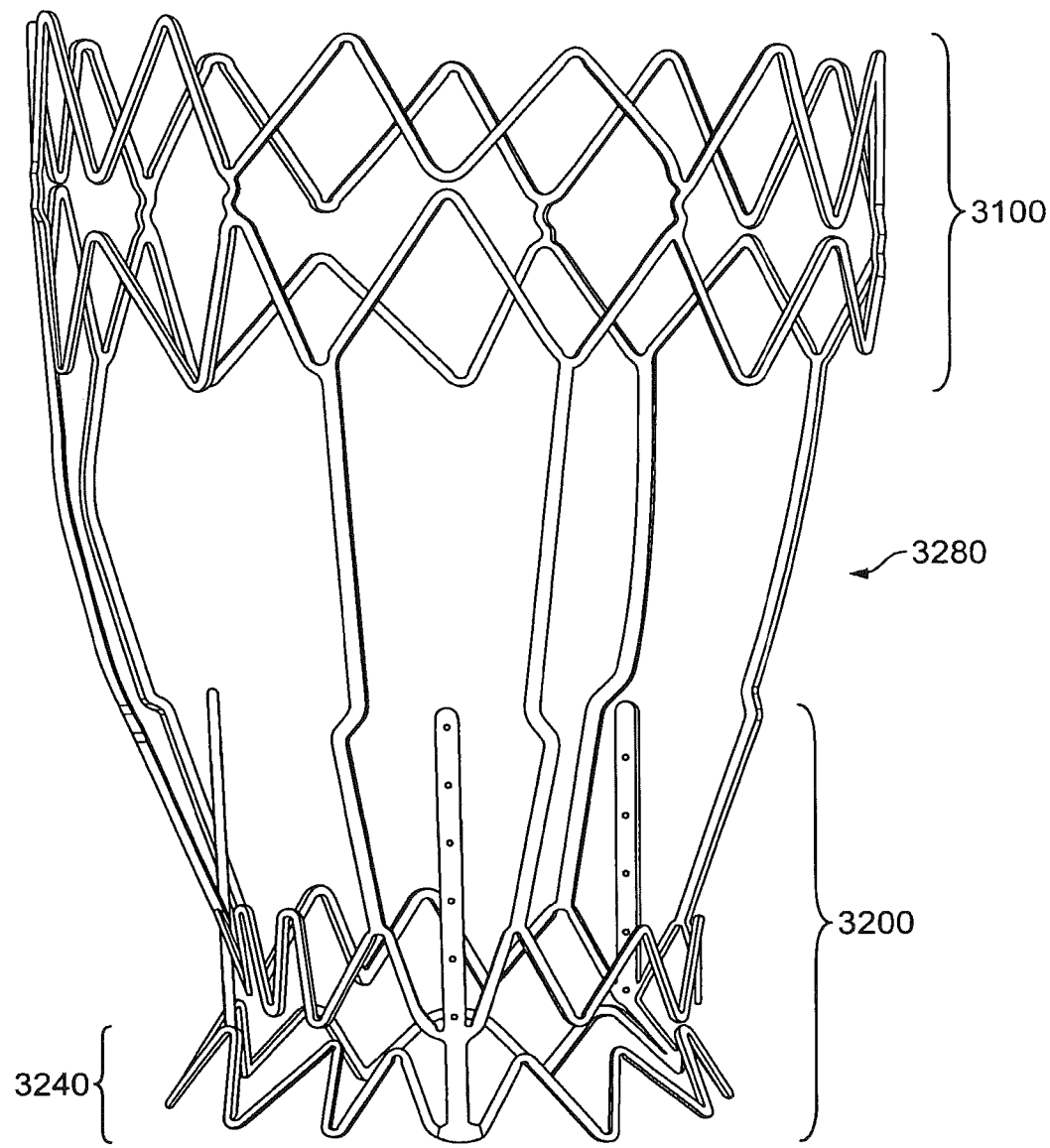
FIG. 18 is similar to FIG. 16, but for the FIG. 17 embodiment.
Figure 19:
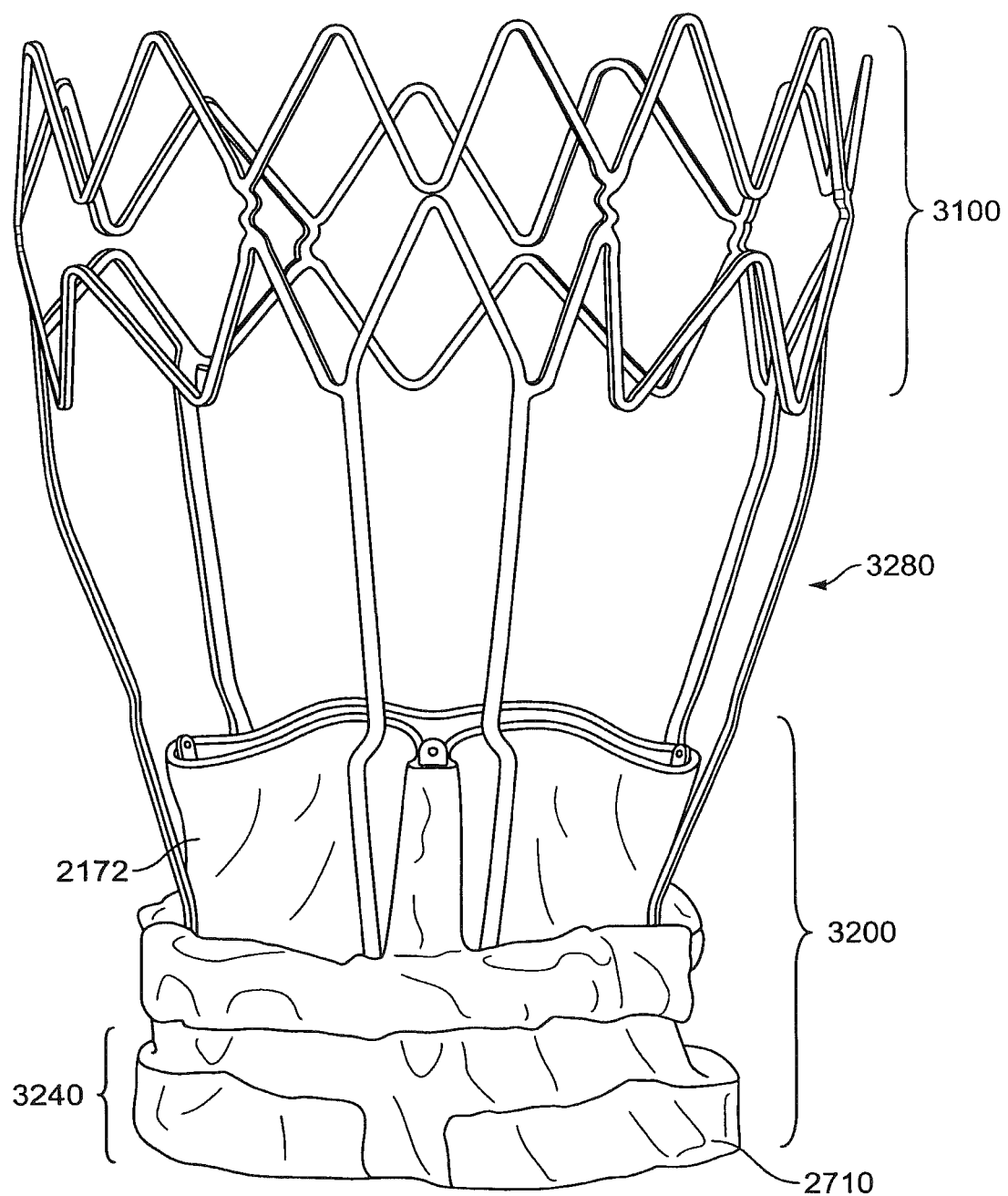
FIG. 19 is similar to FIG. 18, but with some further components added.

FIGS. 17-19 show the primary (tubular or hollow cylindrical) metal component 3010 of still another illustrative embodiment of a prosthetic heart valve in accordance with the invention. Elements in FIGS. 17-19 that are generally similar to previously described elements have reference numbers in FIGS. 17-19 that are increased by 1000, 2000, or 3000 from the reference numbers previously used for the similar elements. Again, to simplify the depiction, FIG. 17 shows component 3010 cut axially along its length and then flattened, but otherwise in the condition that it has when it is annularly compressed or collapsed. FIG. 18 shows component 3010 in the round and in its fully expanded state. FIG. 19 shows component 3010 with cuff fabric 2170 and polymer leaflets 2172 attached to the bottom sections, but with other possible material layers not shown. The design of FIGS. 17-19 allows for leaflet attachment to a single, solid, independent post 3264 in each commissure region, and with apertures 3266 for suture attachment.

Figure 20:
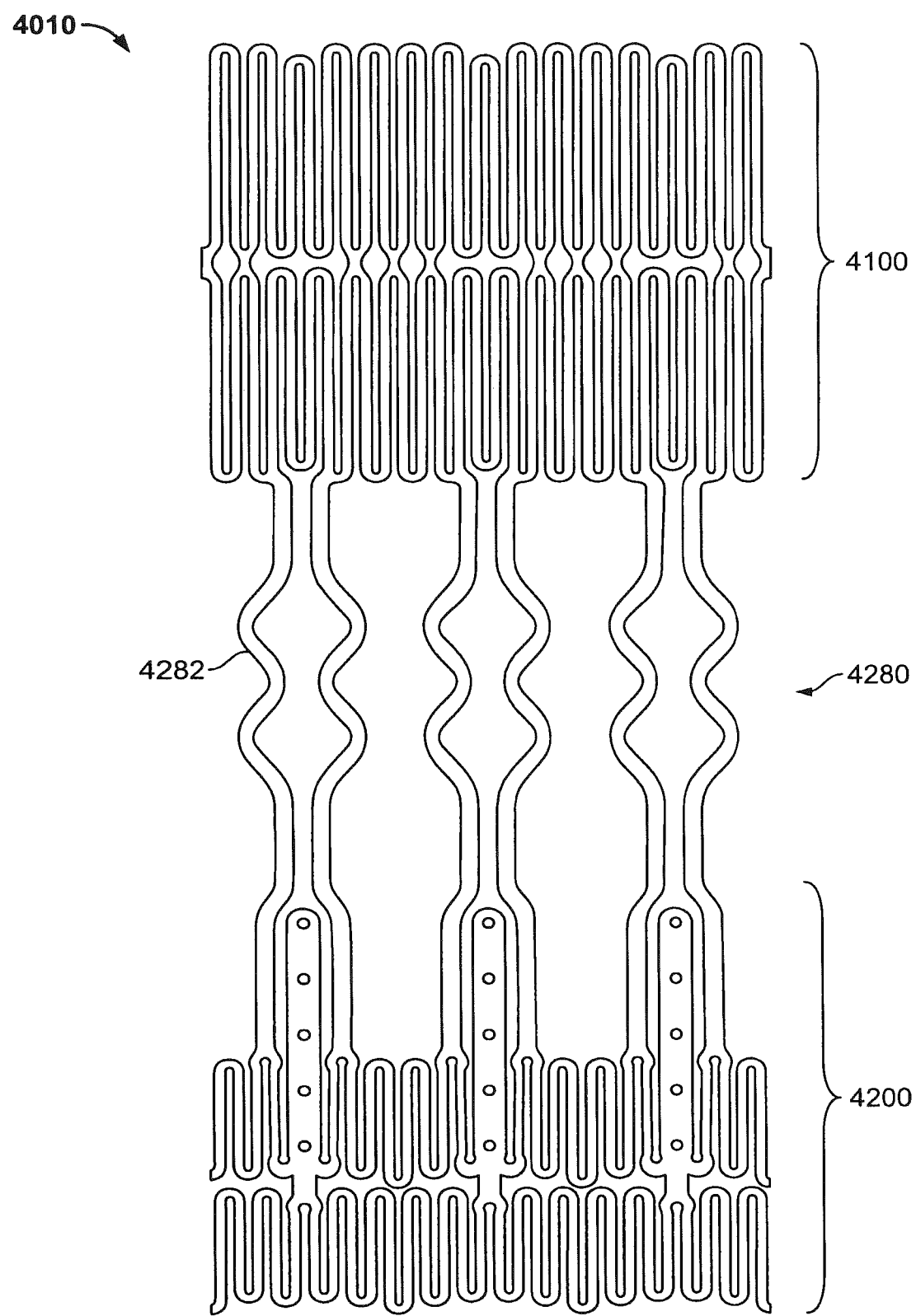
FIG. 20 is similar to FIG. 17 for yet another illustrative embodiment of the invention.

FIG. 20 shows the primary (tubular or hollow cylindrical) metal component 4010 of yet another illustrative embodiment of a prosthetic heart valve in accordance with the invention. Elements in FIG. 20 that are generally similar to previously described elements have reference numbers in FIG. 20 that are increased by 1000, 2000, 3000, or 4000 from the reference numbers previously used for the similar elements. Again, to simplify the depiction, FIG. 20 shows component 4010 cut axially along its length and then flattened, but otherwise in the condition that it has when it is annularly compressed or collapsed. The serpentine shape 4282 of the support struts or linking members 4280 allows for greater flexure and/or extension of the structure between ring portion 4100 and stent portion 4200. This aids in the flexibility of component 4010 within a catheter bending along a tortuous path. It also allows for conformance to bending when this portion of the implanted valve is placed in the ascending aorta where it begins to arch. It also helps to accommodate pulsatile expansion/contraction of the aorta. Shapes 4282 are serpentine by virtue of undulation in directions that are annular of the valve as one proceeds along those shapes in the axial direction (i.e., from element 4100 to element 4200 or vice versa, which could also be described as parallel to the axis of blood flow through the finished and implanted valve).

Figure 21:
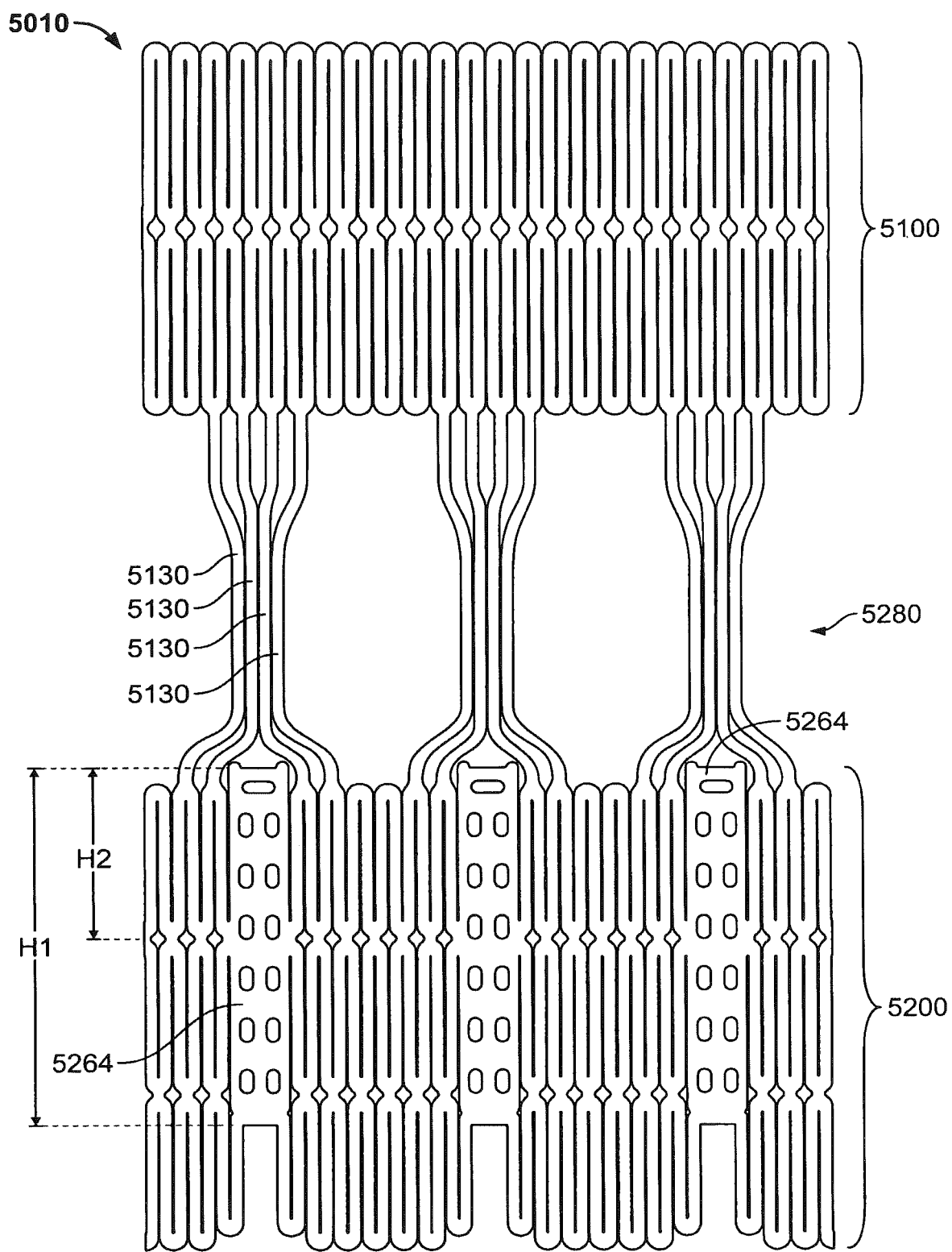
FIG. 21 is similar to FIG. 20 for still another illustrative embodiment of the invention.

FIG. 21 shows the primary (tubular or hollow cylindrical) metal component 5010 of still another illustrative embodiment of a prosthetic heart valve in accordance with the invention. FIG. 21 is the same general kind of drawing as a FIG. 20. Again, reference numbers are increased by multiples of 1000 for generally similar features from earlier-described embodiments. FIG. 21 illustrates the point that ring portion 5100 may be connected to stent portion 5200 by more than two strut members 5130 adjacent each commissure post 5264. In particular, in this embodiment there are four side-by-side struts 5130 adjacent each commissure post 5264. FIG. 21 also shows an example of a structure in which H2 is about 50% of H1 (generally analogous to the parameters H1 and H2 earlier in this specification). In this type of embodiment H1 is the approximate overall height of a solid commissure post 5264, and H2 is the distance from the top of a commissure post 5264 to the highest connection between the commissure post and a link 5130 to ring portion 5100. FIG. 21 also shows other variations from earlier embodiments, which variations will be self-explanatory from what has already been said.

Figure 22:
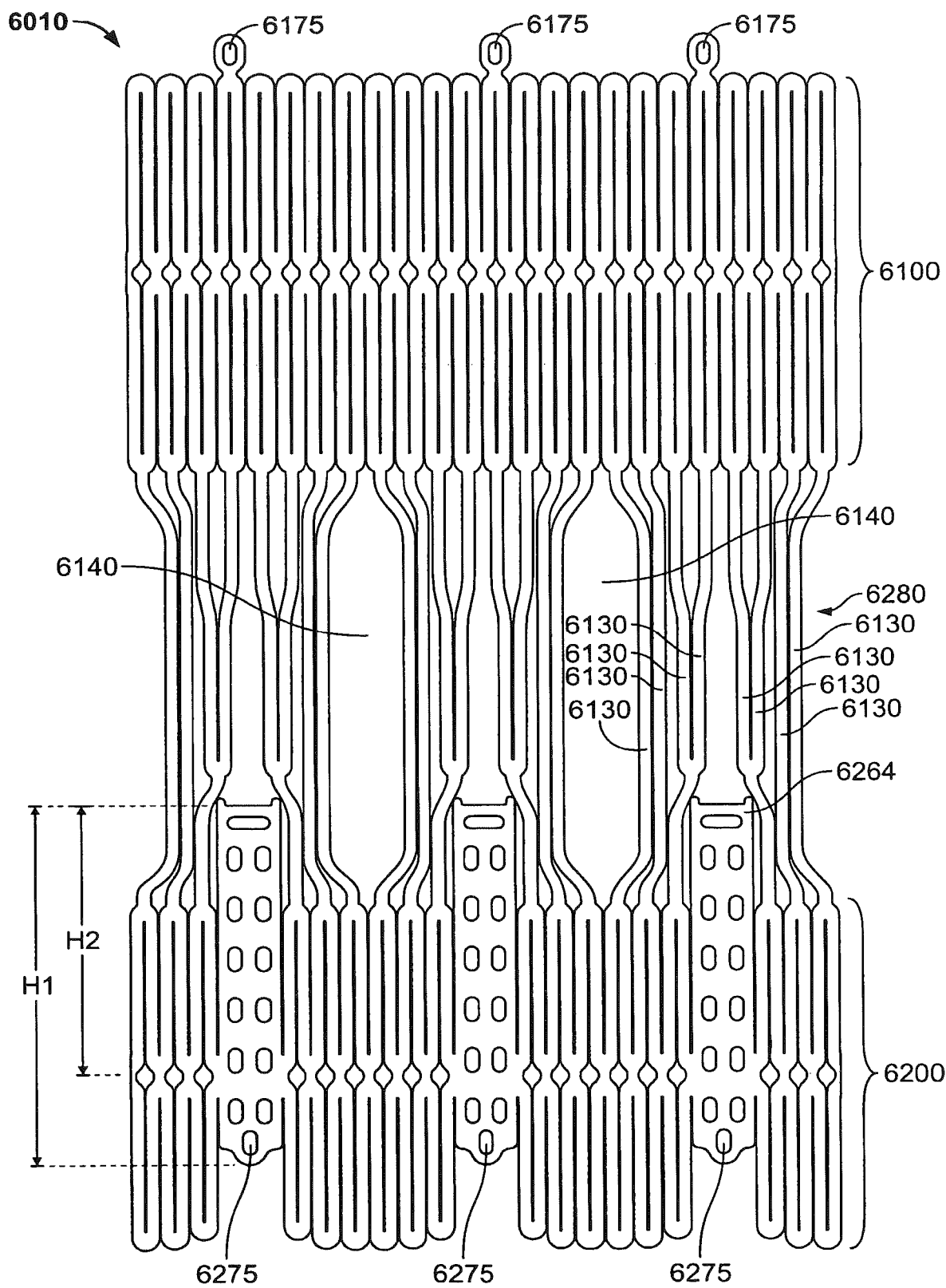
FIG. 22 is similar to FIG. 21 for yet another illustrative embodiment of the invention.

FIG. 22 is similar to FIG. 21 for yet another illustrative embodiment 6010. In FIG. 22 there are six or eight links 6130 (depending on where the count is taken) between ring portion 6100 and stent portion 6200 adjacent each of solid commissure posts 6264. Nevertheless, this design still has large coronary openings 6140, as is the case for all of the other designs herein. FIG. 22 also illustrates a case in which H2 is approximately 75% of H1, as those parameters are defined in the preceding paragraph. FIG. 22 still further illustrates the provision of eyelets 6175 on aortic ring portion 6100 and eyelets 6275 near the base of each stent post that can be used for such purposes as material (like 300, 700, and/or 8300 elsewhere in this specification) attachment and/or releasable attachment of the valve to delivery apparatus.

Figure 23:
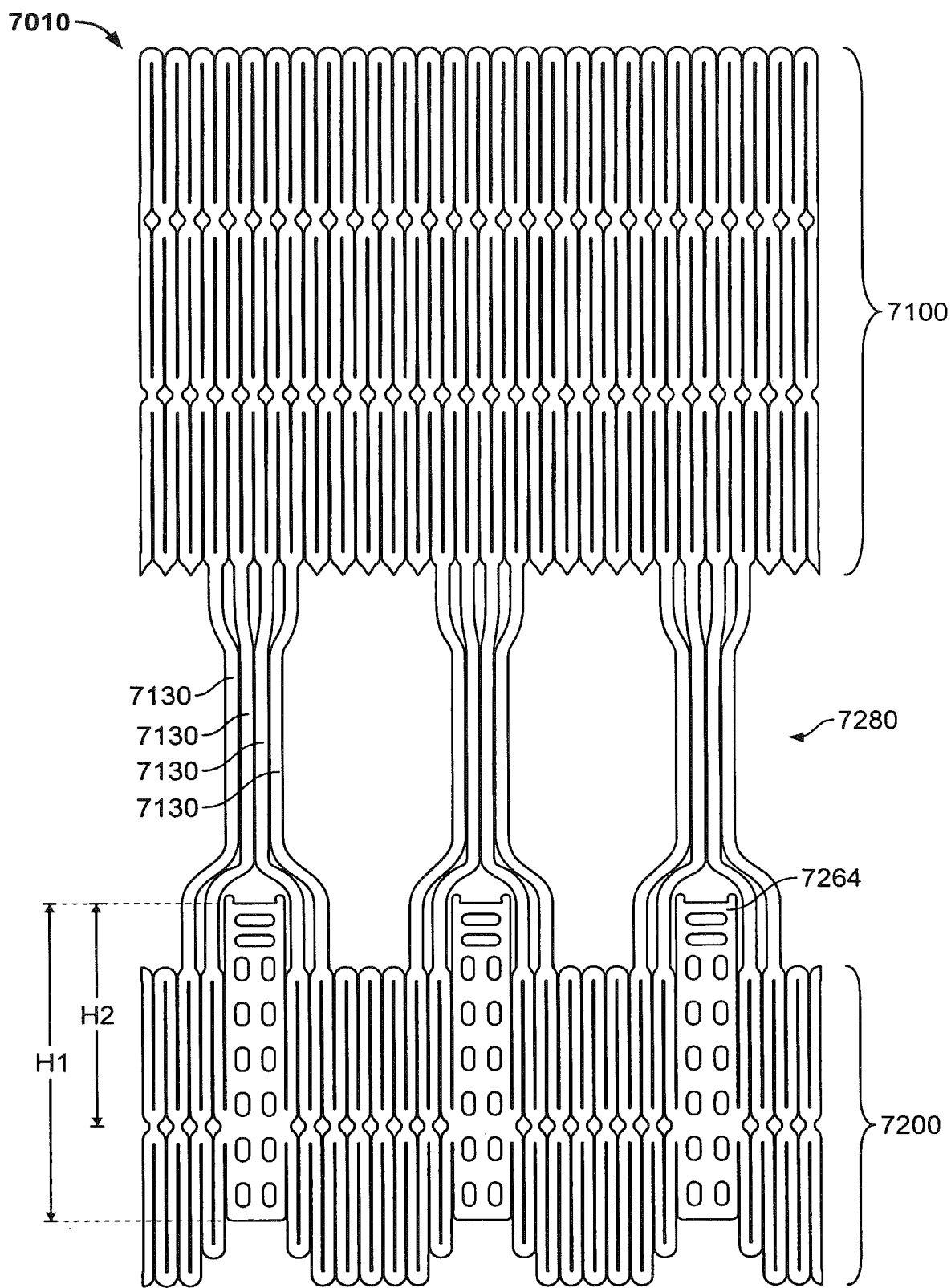
FIG. 23 is similar to FIG. 22 for still another illustrative embodiment of the invention.

FIG. 23 is similar to FIG. 22 for still another illustrative embodiment 7010. In FIG. 23 there are again four links 7130 between ring portion 7100 and stent portion 7200 adjacent each of solid commissure posts 7264. FIG. 23 also illustrates another case in which H2 is nearly 75% of H1, as those parameters are defined in earlier paragraphs.

Figure 24:
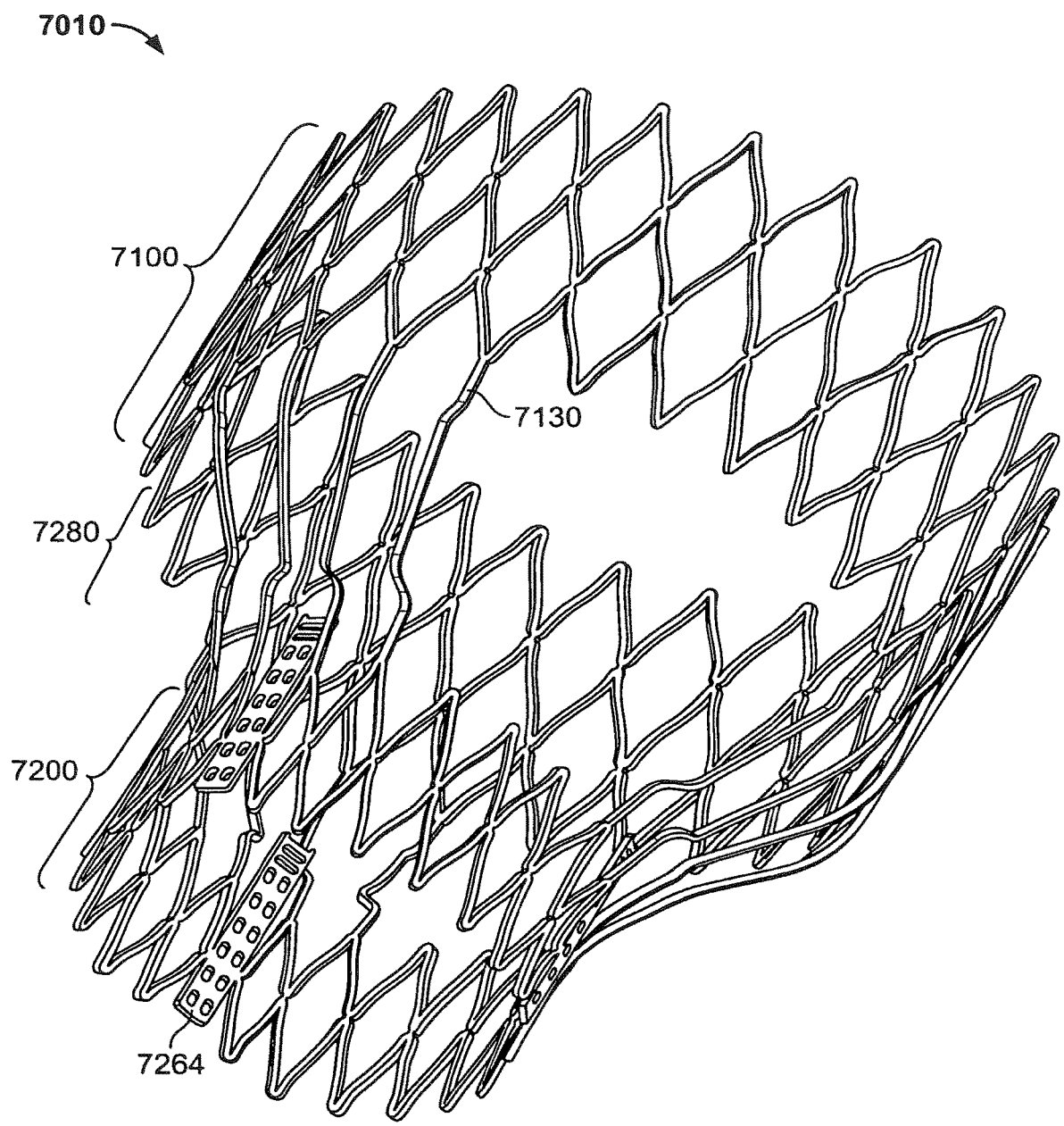
FIG. 24 is a simplified isometric or perspective view showing the FIG. 23 structure in its circumferentially expanded state or condition.

FIG. 24 shows the structure from FIG. 23 in its circumferentially expanded condition or state.

Figure 25:
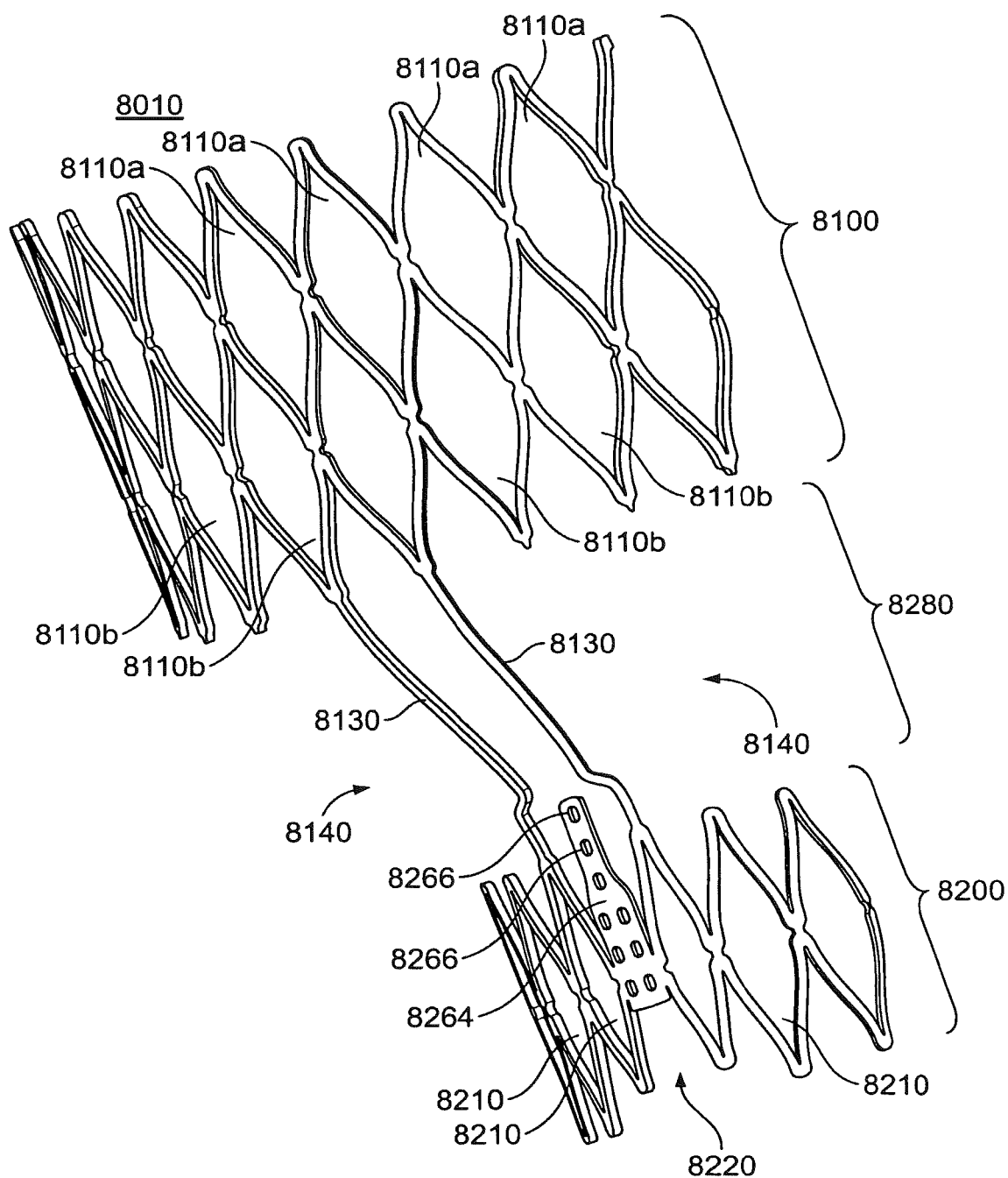
FIG. 25 is a simplified partial isometric or perspective view showing another illustrative embodiment of the invention.

FIG. 25 shows the foreground portion of another illustrative embodiment 8010 in its annularly or circumferentially expanded state or condition. Elements that are generally similar to elements from earlier embodiments have reference numbers that differ by multiples of 1000 from the reference numbers used for those elements in earlier embodiments. Although FIG. 25 shows only the foreground portion of this structure, it will be understood that this structure continues around behind what is shown in FIG. 25 to form a full, continuous, uninterrupted ring structure, just as all of the other embodiments shown herein do. The structure that is visible in FIG. 25 is basically repeated two more times with equal angular spacing as one proceeds all the way around the closed ring structure. As is true for all other embodiments throughout this specification, a prosthetic heart valve that includes structure 8010 is circumferentially collapsible for less invasive delivery into a patient, and then re-expandable (e.g., to the size and shape shown in FIG. 24) when inside the patient at the prosthetic valve implant site in the patient.

In the FIG. 25 embodiment, ring portion 8100 includes two circumferentially extending rows of open-centered, collapsible/expandable cells. The cells in one of these rows have reference number 8110*a*. The cells in the other row have reference number 8110*b*. These two rows are partly overlapping in a direction along a longitudinal axis through the valve (parallel to the direction of blood flow through the valve after it has been implanted and is functioning in a patient). Ring portion 8100 expands to a larger circumferential size than stent portion 8200 as shown in FIG. 25.

Ring portion 8100 and stent portion 8200 are joined to one another by six links or struts 8130 extending between those portions. (Only two of struts 8130 are visible in FIG. 25.) Each pair of two such struts 8130 is located close to a respective one of commissure posts 8264 on stent portion 8200. In particular, each strut 8130 in a given pair is located close to a respective one of the two sides of the associated commissure post 8264. As described for other embodiments earlier in this specification, this leaves relatively large open spaces 8140 in the circumferential direction between adjacent pairs of the struts. Note that struts 8130 flare radially outwardly as one proceeds along the struts from the smaller-circumference stent portion 8200 to the larger-circumference ring portion 8100.

Stent portion 8200 includes a single circumferentially extending row of open-centered, collapsible/expandable cells 8210. This row of cells 8210 is interrupted by solid commissure posts 8264 at three equally spaced locations around the circumference of stent portion 8200. Note that the connections of each commissure post 8264 to the row of cells 8210 are quite low along the overall length of the commissure post. This gives each commissure post 8264 a relatively long, upper, free end portion, along which the commissure post does not have any frame connection to any other portion of valve frame 8010. As in other embodiments considered elsewhere in this specification, this gives most of the length of each commissure post 8264 an independent flexing characteristic. By independent flexing it is meant that the flexing properties of the post can be relatively independently of the flexing properties of the rest of frame (especially the rest of stent portion 8200). For example, each commissure post 8264 can be designed so that its upper free end portion flexes radially inwardly and then radially outwardly in response to each opening/closing cycle of the valve leaflets attached (in part) to that post. The amount of this flexing can be designed into the relatively independent commissure posts relatively independently of the amount of stiffness that it is desired to give the other parts of stent portion 8200 (e.g., for such purposes as to enable the stent portion as a whole to hold back native leaflet tissue, to securely anchor the prosthetic valve in the patient, etc.)

FIG. 25 shows apertures 8266 that can be provided in each commissure post 8264 for the purpose of stitching (suturing) leaflets of the prosthetic valve (and possibly also other layers of tissue or material) to the commissure posts.

In general, it is stated again that for embodiment 8010 (as for other embodiments described throughout this specification) flexible leaflets (like 500 in FIGS. 8 and 9 or like 2172 in FIG. 19) can be attached to stent portion 8200 in the manner generally illustrated elsewhere in this specification. Similarly, it is again stated that for embodiment 8010 (as for other embodiments throughout this specification) other layers of various materials can be attached to various other portions of frame structure 8010 (e.g., as shown at 300, 400, and 700 in FIGS. 6-9 and at 2170 in FIG. 19).

Still another feature that FIG. 25 illustrates is the scalloping of the lower end of stent portion 8200 so that this lower end or edge is relatively high near the bottom of each commissure post 8264 (at reference number 8220) and lower at other locations in the circumferential direction around the valve. This feature is also a characteristic of other embodiments throughout this specification, and it can help the implanted prosthetic valve avoid interfering with other structures in the patient's heart (e.g., the patient's native mitral valve when the prosthetic valve is implanted as a replacement aortic valve).

Figure 26:
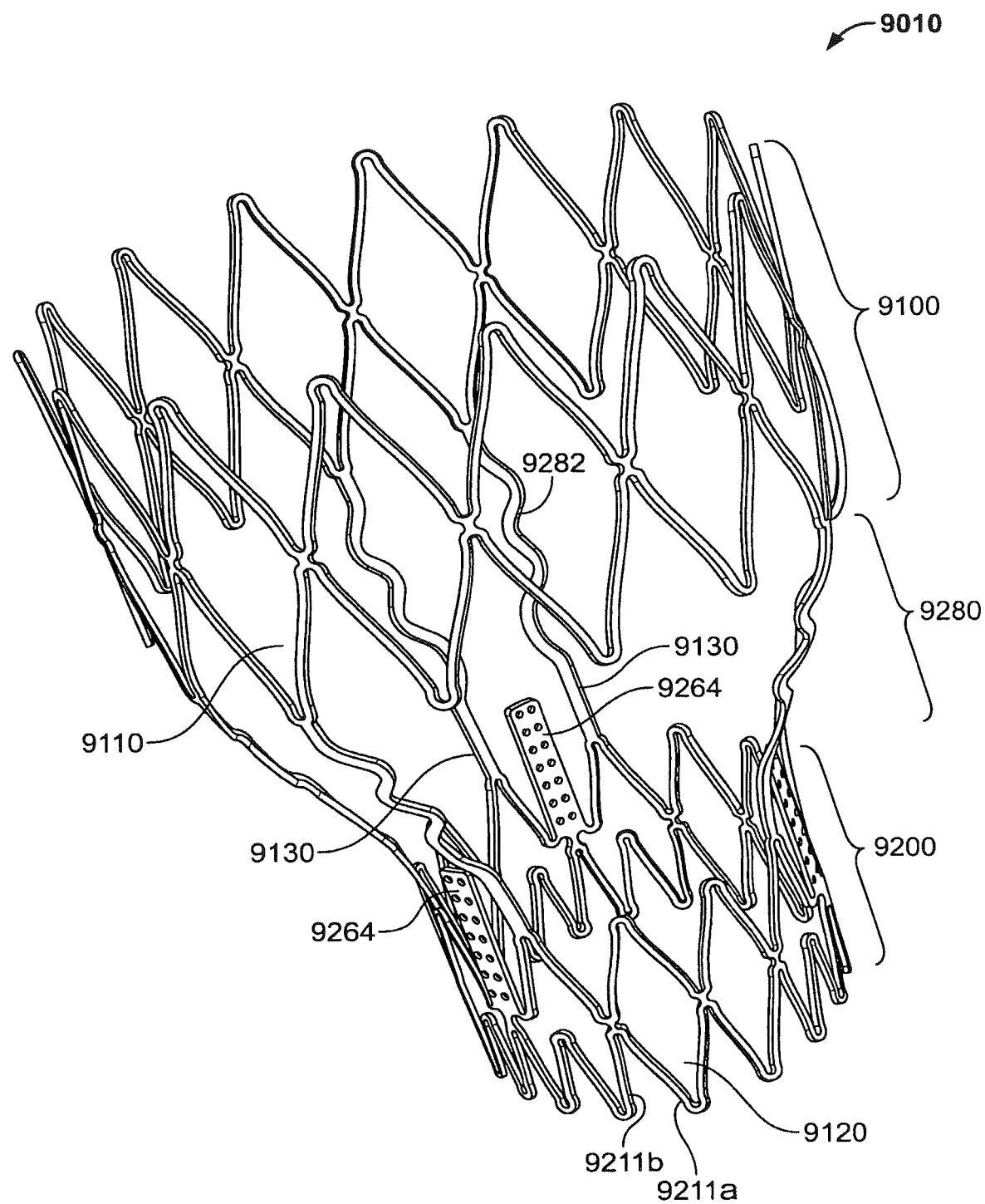
FIG. 26 is similar to FIG. 24 for yet another illustrative embodiment of the invention.

FIG. 26 shows yet another illustrative embodiment 9010. Once again, elements that are generally similar to elements from earlier embodiments have reference numbers that differ by multiples of 1000 from the reference numbers used for those elements in earlier embodiments. As for all other embodiments herein, a prosthetic valve that includes structure 9010 is circumferentially collapsible for less invasive delivery into a patient, and it then re-expands (e.g., as shown in FIG. 26) when at the implant site in the patient. As compared, for example, to FIG. 25, embodiment 9010 has a ring portion 9100 that includes only a single circumferential row of open-centered, collapsible/expandable cells 9110. The stent portion 9200 of embodiment 9010 also includes a single circumferential row of open-centered, collapsible/ expandable cells 9210. However, some of these cells have some sides with extra folds or pleats, which can facilitate giving stent portion 9200 a different geometry, different stiffness in different locations, etc. Examples of such extra folds or pleats are identified by reference numbers 9211a and 9211b. The struts or links 9130 in embodiment 9010 again have serpentine portions 9282 (like 4282 in FIG. 20).

Figure 27:
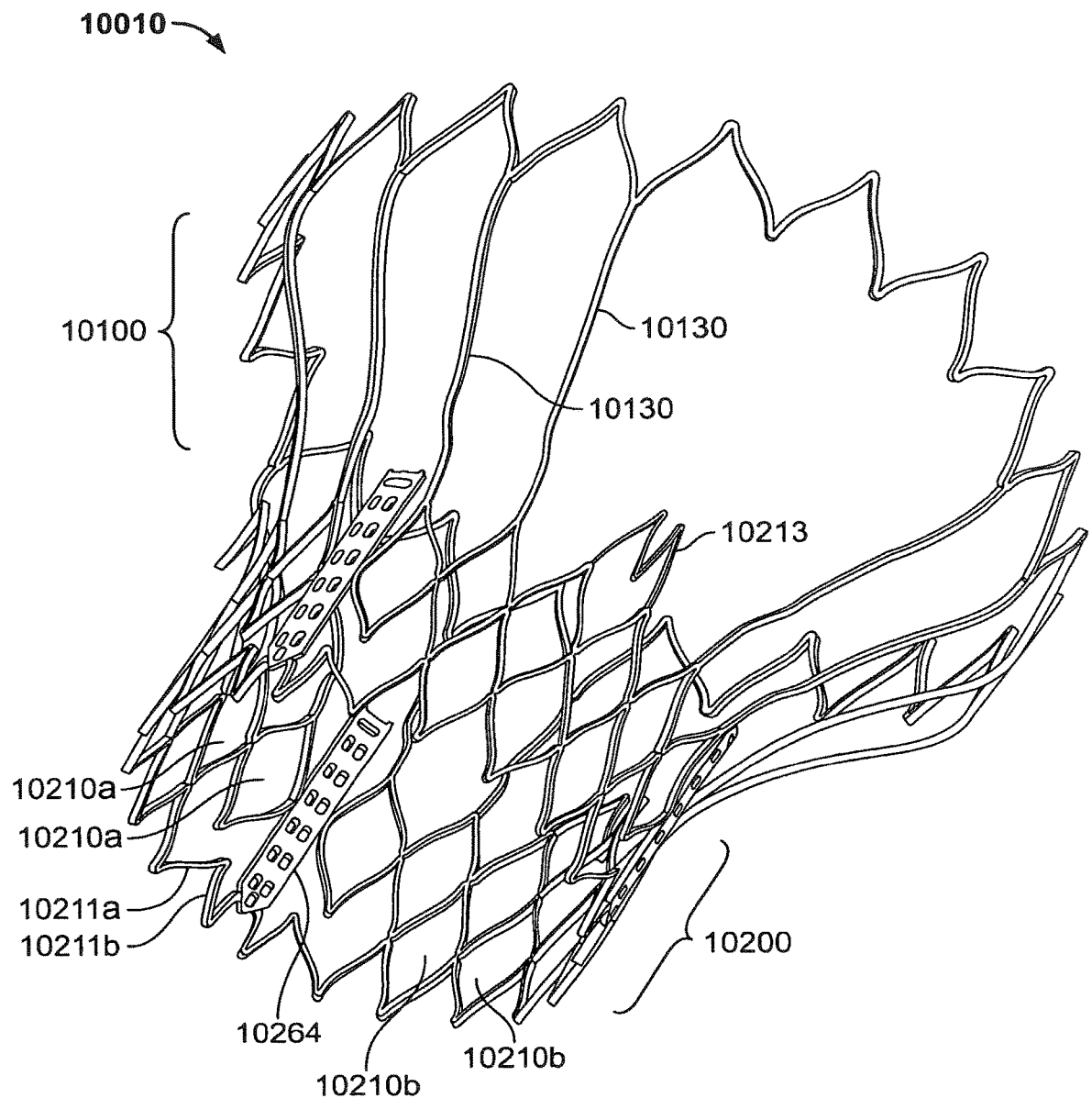
FIG. 27 is similar to FIG. 26 for still another illustrative embodiment of the invention.

FIG. 27 shows still another illustrative embodiment 10010. This embodiment has a stent portion 10200 that includes two circumferentially extending rows of open-centered, collapsible/expandable cells 10210a and 10210b. These two rows partly overlap in the axial direction (i.e., in a direction along a longitudinal axis through the valve). Some of these cells have extra folds or pleats 10211a, 10211b (like 9211a and 9211b in FIG. 26) for reasons similar to what is described above in connection with FIG. 26. The ring portion 10100 of structure 10010 is a single serpentine ring (no open-centered, closed-perimeter cells as in some other embodiments). There are four struts 10130 adjacent each of commissure posts 10264 for connecting ring portion 10100 and stent portion 10200. FIG. 27 is therefore similar to FIGS. 21 and 23 in this respect. Between each group of four struts 10130, stent portion 10200 includes some extra cells 10213 that extend toward ring portion 10100. These structures 10213 can help to hold back native leaflet tissue of the valve that is being replaced by the prosthetic valve and/or to help anchor the prosthetic valve by hooking over the upper edge of the leaflets of the patient's native heart valve.

Figure 28:
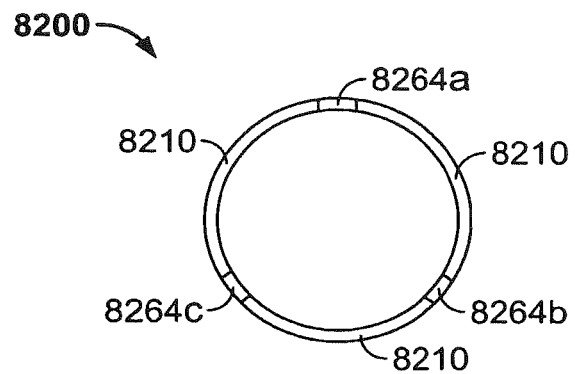
FIG. 28 is a simplified view looking down on a lower part of the structure shown in FIG. 25.

FIG. 28 and several subsequent FIGS. provide additional information as to how valves in accordance with this invention may be constructed. FIG. 28 is a greatly simplified view looking down on the stent portion 8200 of valve frame embodiment 8010 before any other elements have been added to the valve frame. Embodiment 8010 is selected for use in FIG. 28 and subsequent FIGS. solely as an example. Other frame embodiments shown elsewhere herein can be used instead if desired. FIG. 28 shows that stent portion 8200 forms a closed ring, with commissure posts 8264a-c spaced equally from one another around the ring and connected to one another by the inter-commissure row or rows of collapsible/expandable cells 8210. FIG. 28 shows this structure in its circumferentially expanded condition. In embodiments of this general type, all of the circumferential collapse and re-expansion of the valve is provided by cellular structure(s) like 8210 (or in some embodiments, serpentine structure(s)). Commissure posts 8264 are "solid" and therefore not themselves (individually) circumferentially collapsible or re-expandable.

Figure 29:
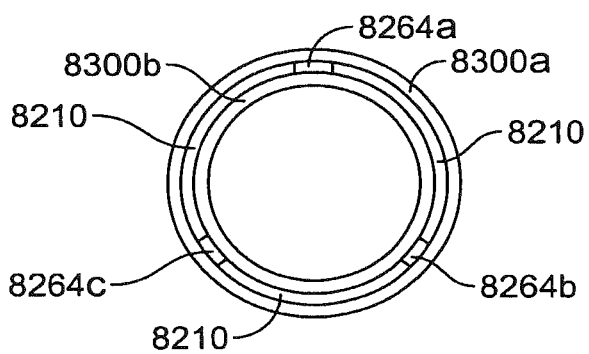
FIG. 29 is a simplified view similar to FIG. 28 with an illustrative embodiment of possible further components added in accordance with the invention.

FIG. 29 shows the addition of one or more layers of flexible, web-like or sheet-like material annularly around the inside and/or outside of stent portion 8200. For convenience herein, all of such sheet material may be referred to by the general reference number 8300. In the particular example shown in FIG. 29, sheet material on the outside of stent portion 8200 has reference number 8300a and sheet material on the inside of stent portion 8200 has reference number 8300b. Sheet material 8300 may be like any of earlier described material(s) 300, 400, 700, and/or 2170. See also FIG. 32, which shows by dotted lines 8300 the upper and lower edges or limits of the sheet material on stent portion 8200 (now shown flat and only in part). Sheet material 8300 may not need to be provided over both the inner and outer surfaces of stent portion 8200, but that is one preferred arrangement. Sheet material 8300 may be secured to stent portion 8200 by sutures that pass through the sheet material and also through and/or around various parts of stent portion 8200. Among the important functions of sheet material 8300 are to help the valve seal the native valve annulus when the valve is implanted in a patient, and to help provide a seal between the prosthetic valve leaflets and the stent or annular portion of the valve.

Figure 33:
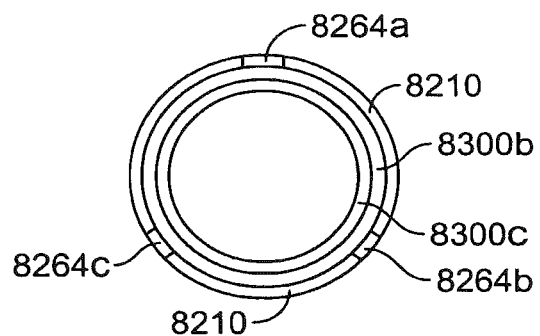
FIG. 33 is similar to FIG. 29 for another illustrative embodiment in accordance with the invention.
Figure 34:
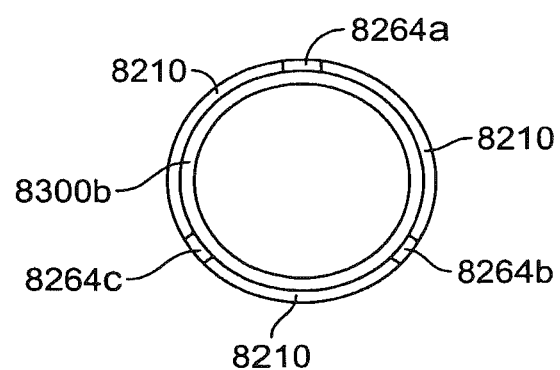
FIG. 34 is again similar to FIG. 29 for yet another illustrative embodiment in accordance with the invention.

Some examples of possible variations of what is described in the immediately preceding paragraph are shown in FIGS. 33 and 34. FIG. 33 shows an illustrative embodiment with two layers of sheet material 8300b and 8300c inside stent structure 8210/8264. In such an embodiment, inner-most layer 8300c may be adapted for buffering and sealing of the flow of blood (especially in the pockets that are formed by leaflets 500 in the interior of the valve). Thus, for example, inner-most layer 8300c may be made of tissue. Outer layer 8300b may be adapted for sealing with the patient's native anatomy and/or tissue in-growth from that anatomy. Outer layer 8300b may therefore be made of a fabric material.

FIG. 34 shows an illustrative embodiment with only one layer of sheet material 8300b inside stent structure 8210/ 8264.

Figure 30:
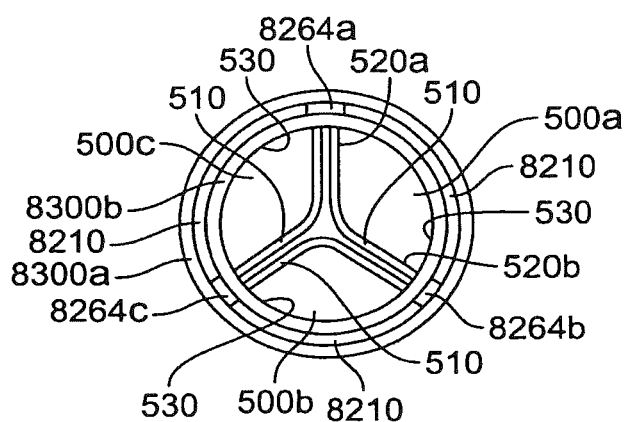
FIG. 30 is a simplified view similar to FIG. 29 with an illustrative embodiment of still more components added in accordance with the invention.
Figure 31:
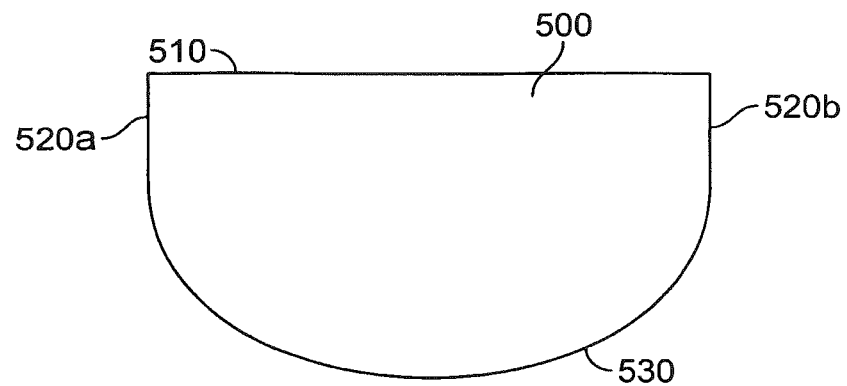
FIG. 31 is a simplified elevational view of an illustrative embodiment of a component that can be used in valves in accordance with the invention.

FIG. 30 shows addition of three, flexible, prosthetic valve leaflets 500a c to the FIG. 29 structure. A representative one of these leaflets, prior to incorporation into the prosthetic valve, is shown by itself in FIG. 31. As shown in FIG. 31, each leaflet 500 may start as a flat sheet. The upper straight or relatively straight edge 510 of this sheet becomes the free edge of the leaflet when the leaflet is assembled in the prosthetic valve. Two approximately straight, upper, side edge portions 520a b of the leaflet can be attached, respectively, to two of the commissure posts 8264 of the prosthetic valve. The arcuate lower edge portion 530 of the leaflet can be attached (at least partly) to material 8300 between the immediately above-mentioned two commissure posts 8264. All of reference numbers 510, 520, and 530 are shown in FIG. 30 for a representative one of the leaflets, but to avoid over-complicating that FIG., only reference numbers 510 and 530 are shown for the two other leaflets.

Figure 35:
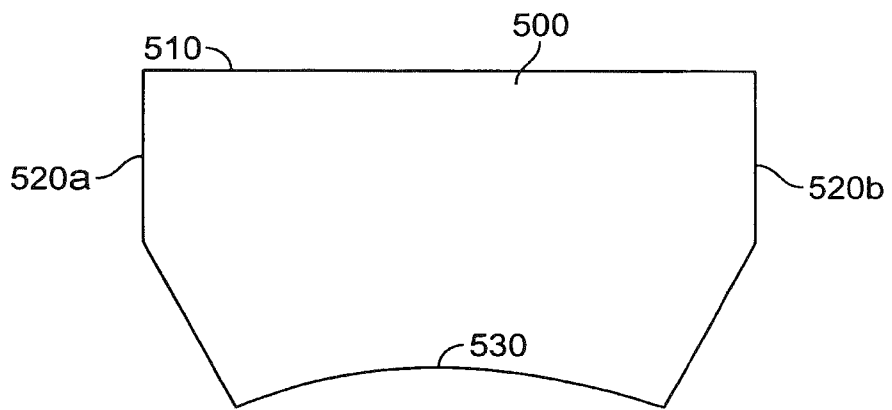
FIG. 35 is similar to FIG. 31 for another illustrative embodiment in accordance with the invention.
Figure 36:
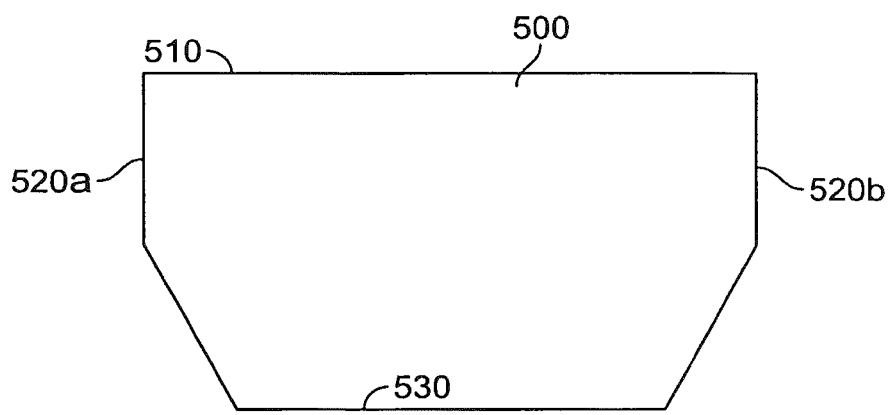
FIG. 36 is again similar to FIG. 29 for still another illustrative embodiment in accordance with the invention.

FIG. 35 shows an alternative embodiment in which the lower edge 530 of leaflet 500 arches up rather than down as in FIG. 31. FIG. 36 shows another alternative embodiment in which the lower edge 530 of leaflet 500 is approximately straight across. The leaflet shape that is chosen depends on the operational characteristics it is desired to achieve. For convenience, the edge portion 530 that is generally opposite free edge 510 may sometimes be referred to as the secured edge portion of the leaflet.

Figure 32:
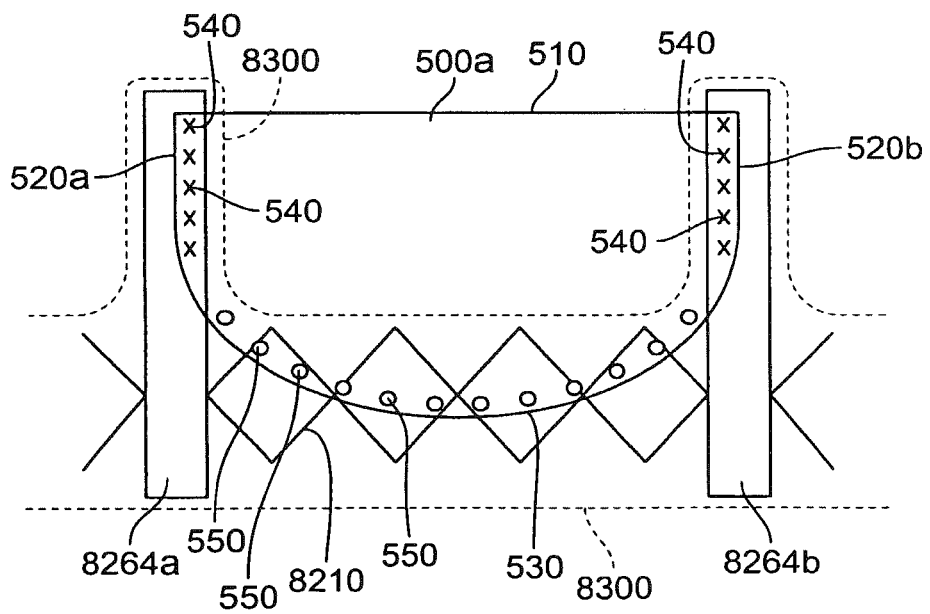
FIG. 32 is a simplified side view (flattened out to a plane) of an illustrative embodiment of a representative portion of what is shown in FIG. 30 in accordance with the invention.

FIG. 30 shows the valve in the closed condition. The "free" upper edges 510 of the three leaflets 500a c come together in approximately a Y shape in the interior of the valve to provide a fluid seal between the leaflets. The side edges 520a b and the lower edge 530 of each leaflet are secured to the annular structure 8200/8300 of the valve in a way that provides a seal between each leaflet and the adjacent portion of the annular structure. For example, this may be accomplished by stitching (suturing) edges 520 and 530 of each leaflet to the annular structure as illustrated by FIG. 32. In that FIG., "x" marks 540 are used to indicate where side edge portions 520 of a typical leaflet 500 may be stitched (sutured) to cantilevered free end portions of commissure posts 8264 (e.g., through commissure post apertures 8266 (FIG. 25)). This stitching may additionally pass through material 8300. But even if there is material 8300 between a leaflet 500 and a commissure post 8264, the stitching 540 is preferably directly (straight) through the leaflet and through or to the commissure post so that the stitching 540 can apply force from the leaflet directly to the commissure post. Also in FIG. 32, "o" marks 550 are used to indicate where the bottom edge of a typical leaflet 500 may be stitched at least in part to the material 8300 that spans the open-cellular, inter-commissure structure 8210 of stent portion 8200 (between commissure posts 8264). The net result of all of this construction is to seal the entire side and lower perimeter 520/530 of each leaflet 500 to the annular structure 8200/8300 of the valve, while leaving the upper edges 510 of the leaflets with sufficient slack to come together (as shown in FIG. 30) to close the valve (or to move apart to open the valve).

The above-described continuous seal of leaflets 500 to the annular structure (especially 8300) is effectively continued (by continuous annular web material 8300) to the native valve annulus by stent portion 8200 pressing sheet material 8300 radially outwardly into annular sealing contact or engagement with the native valve annulus.

Continuous sheet material 8300 provides many more places 550 where the lower edges of leaflets 500 can be stitched to annular structure 8200/8300 than would be provided by relatively widely spaced frame elements 8210 alone. This improves sealing between the leaflets and the annular structure. (Some of stitches 550 may also directly embrace (e.g., wrap around) elements of frame structure 8210. But others of stitches 550 typically pass through only a leaflet 500 and sheet material 8300.) Similarly, the continuous nature of sheet material 8300 improves sealing between annular structure 8200/8300 and the patient's native valve annulus. On the other hand, being able to secure (suture/stitch) the upper side edges 520 of each leaflet 500 substantially directly to commissure posts 8264 (e.g., at locations 540) is desirable because these upper portions of the leaflet may tend to try to pull away from annular structure 8200/8300 as the valve opens and closes. Therefore, strong and relatively direct leaflet-to-commissure-post attachment at points 540 is desirable to absorb this cyclical tension at the ends of the upper free edge of each leaflet. The cantilevered, upper, free end portions of commissure posts 8264 can flex radially in and out in spring-like fashion to absorb the shock of this cycling leaflet tension and to reduce the maximum amplitude value that this tension reaches in its cycle. Because the free end portions of commissure posts 8264 are cantilevered from the rest of valve frame 8010, these portions of the commissure posts can be given any desired degree of flexibility or stiffness independent of the stiffness or flexibility designed into other parts of the valve frame.

Note that the prosthetic valve is preferably built up (constructed) from components that are initially separate as follows: (1) frame 8010, (2) sheet material 8300, and (3) leaflets 500. Further note that the order of assembly is typically as follows: (1) frame 8010 is provided, (2) sheet material 8300 is added to frame 8010, and (3) leaflets 500 are added inside the assembly of elements 8010 and 8300. Amplifying this last point somewhat, the three leaflets 500 may be stitched together side-edge-to-side-edge prior to immediately above-mentioned step (3). Then above-mentioned step (3) may include (a) dropping the assembly of leaflets into place inside annular structure 8200/8300, (b) suturing the leaflets individually to each commissure post 8264 (e.g., at locations 540), and (c) suturing the belly of each leaflet to sheet material 8300 (e.g., at locations 550) to form the actual valve. Those skilled in the art will appreciate that variations on this are possible. In general, however, it is typically the case that no valve exists separate from frame structure 8010, or prior to addition of elements 8300 and 500 to frame structure 8010.

Again, it is expressly stated that FIGS. 28-32 and the immediately above paragraphs refer to frame embodiment 8010 only as an example, and that these principles are equally applicable to other embodiments shown and described elsewhere in this specification.

To quantify what is meant by valves of this invention being collapsible and re-expandable, it is preferred that a diameter of a valve in accordance with this invention be collapsible by at least about 50% (e.g., from about 20-30 mm when fully expanded to about 10-15 mm when fully collapsed). All of the valves shown herein are capable of collapsing by amounts typified by what is said in the immediately preceding sentence. More preferably, the percentage of such diameter reduction when the valve is collapsed is in the range from about 60% to about 80% (e.g., to about 5-10 mm for a 25 mm expanded valve). At least the valves shown in the FIGS. from FIG. 12 to the end are capable of collapsing by amounts typified by what is said in the immediately preceding sentence. Note that a 60% diameter reduction means that the diameter of the collapsed valve is 40% of the diameter of the expanded valve. An 80% diameter reduction means that the diameter of the collapsed valve is 20% of the diameter of the expanded valve.

From the foregoing it will be appreciated that the valves of this invention can be reduced in circumferential size (e.g., for less invasive delivery of the valve into a patient) and then re-expanded to full (or normal) circumferential size at the valve-implant site in the patient. The valves of this invention typically change circumference in this way without otherwise radically changing in shape. Reduction in circumference may be accompanied by a temporary increase in length of the valve. Also, a skirt like 240, 1240, etc., that is resiliently biased to deflect radially out may be temporarily deflected in. But the tubular or cylindrical outer periphery of the valve (e.g., structure 10, 1010, 2010, 3010, or 4010) preferably always remains tubular or cylindrical. It preferably does not undergo any radical shape change such as would be involved if it were folded, creased, or wound along the length (blood flow axis) of the valve. The circumference of the valve is reduced by compression of component 10, 1010, etc., in the annular or circumferential direction, which leaves component 10, 1010, etc., a tube of the same basic shape (although of different size) at all times. This type of reduction of the circumferential size of component 10, 1010, etc., (and therefore the remainder of the valve structure), and which does not rely on folding of component 10, 1010, etc., along its length or winding of that component about a longitudinal axis, may be referred to herein as annular or circumferential collapsing, compression, shrinking, reduction, or the like.

In the above discussion it is said that ring 100, 1100, 2100, etc., is connected to stent 200, 1200, 2200, etc., substantially solely by strut structures 280, 1280, 2280, etc., that are adjacent to the commissure posts or tips 236, 1236, 2236, etc. A purpose of this is to leave relatively large openings 140, 1140, 2140, etc. between annularly adjacent pairs of the strut structures. To quantify what is meant by the phrase adjacent to the commissure posts in this context, it can be said that in any given valve, openings 140, 1140, 2140, etc. collectively (preferably) constitute about two-thirds (or an even larger fraction) of the distance in the annular direction around the valve at the height of the commissure tips when the valve is expanded. Thus, for example, in the first-described embodiment, W1 (FIG. 3) is the width of one representative opening 140 at the level of commissure tips 236. W2 is the width of one representative strut structure 130, etc., at that same level. The sum of dimension W1 for all three openings 140 is at least two-thirds the circumference of the fully expanded valve at the level of the commissure tips. The sum of dimension W2 for all three strut structures is less than one-third that valve circumference. This means that the components of each strut structure are relatively close to the adjacent commissure post or tip.

It will be understood that the foregoing is only illustrative of the principles of this invention, and that various modifications can be made by those skilled in the art without departing from the scope and spirit of the invention. For example, the number and shapes of the various cells (like 110 and 210) in component 10 or the like can be different from the number and shapes of the cells shown in the FIGS. herein. Similarly, the number of undulations in serpentine structures such as 1160a, 1160b, 1162, or the like can be different from the numbers shown in the FIGS. herein.

The invention claimed is:

1. A prosthetic heart valve, comprising:
   a collapsible and expandable stent component formed of a shape-memory alloy, the stent component including a generally tubular first stent portion and a generally tubular second stent portion, the first stent portion having an expanded diameter that is greater than an expanded diameter of the second stent portion;
   a plurality of valve leaflets coupled directly to the second stent portion but not directly to the first stent portion, the plurality of valve leaflets configured to allow blood to flow in a downstream direction, but to restrict blood from flowing in an upstream direction;
   a first fabric at least partially covering an exterior surface of the first stent portion; and
   a plurality of barbs coupled to the first stent portion and extending in the upstream direction, the plurality of barbs configured to pierce tissue to prevent migration of the prosthetic heart valve in the upstream direction,
   wherein the first stent portion is coupled to the second stent portion to form an independent stent-in-stent design.

2. The prosthetic heart valve of claim 1, wherein the first stent portion is coupled to the second stent portion via a plurality of individual attachment links that are positioned at spaced locations around a circumference of the stent component.

3. The prosthetic heart valve of claim 1, wherein the first stent portion includes at least one circumferential row of closed-perimeter cells.

4. The prosthetic heart valve of claim 3, wherein the closed-perimeter cells are diamond-shaped.

5. The prosthetic heart valve of claim 4, wherein at least a portion of the plurality of barbs is uncovered by the first fabric to allow the plurality of barbs to embed into tissue.

6. The prosthetic heart valve of claim 5, wherein in the expanded condition of the prosthetic heart valve, an inflow end of stent component flares radially outwardly from a central longitudinal axis of the prosthetic heart valve.

7. The prosthetic heart valve of claim 1, wherein the first fabric is a polyester.

8. The prosthetic heart valve of claim 1, wherein the shape-memory alloy is nitinol.

9. The prosthetic heart valve of claim 1, wherein the second stent portion is at least partially covered by a second fabric.

10. The prosthetic heart valve of claim 9, wherein the second fabric is formed of a polyester.

11. The prosthetic heart valve of claim 10, wherein the second fabric covers an interior and an exterior of the second stent portion.

12. The prosthetic heart valve of claim 1, wherein the first stent portion is spaced from the second stent portion such that the plurality of valve leaflets cannot contact the first stent portion during operation of the prosthetic heart valve.

13. The prosthetic heart valve of claim 1, wherein the first stent portion is substantially concentric with the second stent portion.

14. The prosthetic heart valve of claim 1, wherein the second stent portion includes three commissure regions, the plurality of valve leaflets being coupled directly to the three commissure regions.

15. The prosthetic heart valve of claim 14, wherein, during operation of the prosthetic heart valve, the three commissures regions are spaced radially inwardly from the first stent portion so that a gap exists between an outer surface of the three commissure regions and an inner surface of the first stent portion.

16. The prosthetic heart valve of claim 14, wherein the independent stent-in-stent design is configured to allow the first stent portion to flex independently of the three commissure regions.

17. The prosthetic heart valve of claim 16, wherein the first stent portion is configured to anchor the prosthetic heart valve within a heart so that the plurality of valve leaflets are positioned within a native valve annulus of the heart.

18. The prosthetic heart valve of claim 17, wherein the prosthetic heart valve is devoid of structures that span directly between the first stent portion and the second stent portion in a manner that constrains independence of motion between the first stent portion and the second stent portion.

* * * * *